United States Patent
Fadli

(10) Patent No.: US 9,271,910 B2
(45) Date of Patent: Mar. 1, 2016

(54) **DYE COMPOSITION COMPRISING A CATIONIC *PARA*-AMINOPHENOL OXIDATION BASE**

(75) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/345,103

(22) PCT Filed: Sep. 13, 2012

(86) PCT No.: PCT/EP2012/067984
§ 371 (c)(1),
(2), (4) Date: Mar. 14, 2014

(87) PCT Pub. No.: WO2013/037907
PCT Pub. Date: Mar. 21, 2013

(65) Prior Publication Data
US 2014/0352081 A1   Dec. 4, 2014

Related U.S. Application Data

(60) Provisional application No. 61/539,112, filed on Sep. 26, 2011.

(30) Foreign Application Priority Data

Sep. 15, 2011 (FR) ...................... 11 58216

(51) Int. Cl.
| | |
|---|---|
| *A61Q 5/10* | (2006.01) |
| *A61K 8/41* | (2006.01) |
| *C07D 295/135* | (2006.01) |
| *A61K 8/49* | (2006.01) |
| *C07C 215/80* | (2006.01) |
| *C07C 217/08* | (2006.01) |
| *C07C 217/84* | (2006.01) |
| *C09B 69/00* | (2006.01) |

(52) U.S. Cl.
CPC . *A61K 8/415* (2013.01); *A61K 8/41* (2013.01); *A61K 8/49* (2013.01); *A61K 8/494* (2013.01); *A61K 8/4913* (2013.01); *A61K 8/4926* (2013.01); *A61K 8/4946* (2013.01); *A61Q 5/10* (2013.01); *C07C 215/80* (2013.01); *C07C 217/08* (2013.01); *C07C 217/84* (2013.01); *C07D 295/135* (2013.01); *C09B 69/001* (2013.01); *A61K 2800/10* (2013.01)

(58) Field of Classification Search
CPC ............. A61Q 5/10; A61K 8/41; A61K 8/49; A61K 8/4946; A61K 8/4926; A61K 8/4913; A61K 8/415; A61K 8/494; C07C 215/80; C07C 217/84; C07C 217/08
USPC ...................... 8/405, 421; 564/443
See application file for complete search history.

(56) References Cited

U.S. PATENT DOCUMENTS

| | | |
|---|---|---|
| RE30,199 E | 1/1980 | Rose et al. |
| 4,823,985 A | 4/1989 | Grollier et al. |
| 5,061,289 A | 10/1991 | Clausen et al. |
| 5,084,067 A | 1/1992 | Junino et al. |
| 5,139,532 A | 8/1992 | Chan et al. |
| 5,364,413 A | 11/1994 | Junino et al. |
| 5,380,340 A | 1/1995 | Neunhoeffer et al. |
| 5,503,640 A | 4/1996 | Junino et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,419,711 B1 | 7/2002 | Genet et al. |
| 6,645,258 B2 | 11/2003 | Vidal et al. |
| 2002/0050013 A1 | 5/2002 | Vidal et al. |
| 2003/0019051 A9 | 1/2003 | Vidal et al. |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0331144 A2 | 9/1989 |
| EP | 0770375 A1 | 5/1997 |

(Continued)

OTHER PUBLICATIONS

STIC Search Report dated Sep. 18, 2014.*

(Continued)

*Primary Examiner* — Eisa Elhilo

(74) *Attorney, Agent, or Firm* — The Marbury Law Group, PLLC

(57) ABSTRACT

The present invention relates to a para-aminophenol compound of formula (I) the addition salts thereof with an acid and the solvates thereof, dye composition comprising the latter and a dyeing process.

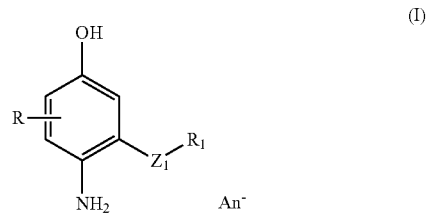

(I)

21 Claims, No Drawings

(56) References Cited

FOREIGN PATENT DOCUMENTS

| | | | |
|---|---|---|---|
| FR | 2586913 | A1 | 3/1987 |
| FR | 2733749 | A1 | 11/1996 |
| FR | 2750048 | A1 | 12/1997 |
| GB | 1026978 | | 4/1966 |
| GB | 1153196 | | 5/1969 |
| JP | 02019576 | | 1/1990 |
| JP | 05163124 | | 6/1993 |
| WO | 9408969 | A1 | 4/1994 |
| WO | 9408970 | A1 | 4/1994 |
| WO | 9615765 | A1 | 5/1996 |
| WO | 9948856 | A1 | 9/1999 |
| WO | 0239970 | A1 | 5/2002 |

OTHER PUBLICATIONS

International Search Report for PCT/EP2012/067984.

* cited by examiner

DYE COMPOSITION COMPRISING A CATIONIC PARA-AMINOPHENOL OXIDATION BASE

CROSS REFERENCE TO RELATED APPLICATIONS

This is a national stage application of PCT/EP2012/067984, filed internationally on Sep. 15, 2011, which claims priority to U.S. Provisional Application No. 61/539,112, filed on Sep. 26, 2011, as well as French Application No. FR. 1158216, filed on Sep. 15, 2011, all of which are incorporated herein by their entireties.

The invention relates to particular novel cationic para-aminophenol compounds, a dye composition comprising the latter and also a dyeing process using these compounds.

It is known practice to dye keratin fibres and in particular human hair with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colour modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" colouring obtained by means of these oxidation dyes must moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in colour along the same keratin fibre, which in general is differently sensitized (i.e. damaged) between its end and its root.

It is already known practice to use oxidation bases of the para-aminophenol type for dyeing keratin fibres, especially the hair. For example, 3-substituted para-aminophenol oxidation bases are known from document EP 0 331 144. These bases may have the drawbacks of resulting in colourings that are not sufficiently intense or chromatic and/or that are too selective.

The aim of the present invention is to obtain a hair dye composition that has improved dyeing properties in terms of intensity or chromaticity and/or selectivity and/or resistance to external agents.

Surprisingly and advantageously, the Applicant has just discovered a new family of oxidation bases constituted of cationic para-aminophenols. These bases result in a wide range of colours in oxidation dyeing. They make it possible in particular to expand the colour range while improving the harmlessness of the oxidation bases. Furthermore, these cationic para-aminophenols make it possible to obtain colourings having varied shades and that are powerful and chromatic.

One subject of the invention is therefore a para-aminophenol compound of formula (I) below, the addition salts thereof and the solvates thereof:

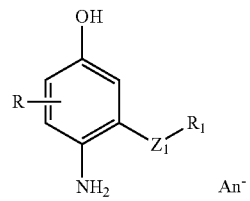

in which:
R represents a hydrogen or halogen atom; a $C_1$-$C_4$ alkyl radical; a carboxyl radical or a ($C_1$-$C_4$)alkoxycarbonyl radical;
Z1 is an oxygen atom or a group NR2;
R2 is a hydrogen atom or a linear or branched $C_1$-$C_4$ alkyl radical, a benzyl radical or an acetyl radical;
R1 is a saturated, linear or branched $C_1$-$C_{10}$ alkyl radical, which is substituted with or interrupted by a cationic radical, optionally interrupted by one or more oxygen atoms and/or by one or more groups NR2, optionally substituted with one or more radicals chosen from hydroxyl, alkoxy or $C_1$-$C_4$ hydroxyalkyl radicals;
or
R1 is a saturated, unsaturated or aromatic cationic 5- to 8-membered heterocycle optionally substituted with one or more radicals chosen from $C_1$-$C_4$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido or $C_1$-$C_4$ hydroxyalkyl radicals;
and
when Z1 represents NR2 then
R1 and R2 may form, together with the nitrogen atom to which they are attached, a saturated or unsaturated cationic 5- to 8-membered heterocycle optionally substituted with one or more radicals chosen from $C_1$-$C_{10}$ alkyl radicals and hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals, it being possible for this heterocycle to contain one or more heteroatoms chosen from N or O, preferably N;
or
R1 and R2 may form, together with the nitrogen atom to which they are attached, a saturated or unsaturated non-cationic 5- to 8-membered heterocycle substituted with a cationic radical and optionally substituted with one or more radicals chosen from $C_1$-$C_{10}$ alkyl radicals and hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals;
An⁻ represents an anion or a mixture of anions which are organic or inorganic and are cosmetically acceptable.

Another subject of the invention is a composition for dyeing keratin fibres, comprising, in a suitable dyeing medium, as an oxidation base, at least one para-aminophenol compound as defined above. Another subject of the invention is a process for dyeing keratin fibres using this composition.

Another subject of the invention is the use of the composition of the present invention for dyeing keratin fibres, in particular human keratin fibres such as the hair.

The invention also relates to multi-compartment devices comprising compositions containing one or more oxidation bases chosen from the compound of formula (I) or an addition salt thereof with an acid.

A final subject of the invention is a dyeing kit comprising, on the one hand, a dye composition containing an oxidation base of formula (I) and, on the other hand, a composition containing an oxidizing agent.

The compounds of the present invention make it possible in particular to obtain compositions for dyeing keratin fibres that are suitable for use in oxidation dyeing and that make it possible to obtain a hair colouring that has improved dyeing properties in terms of intensity or chromaticity and/or selectivity and/or resistance to external agents such as shampoo, sweat, permanent reshaping and light.

For the purposes of the present invention, and unless otherwise indicated:
- an "alkyl radical" is a linear or branched $C_1$-$C_{20}$ and preferably $C_1$-$C_8$ hydrocarbon-based radical;
- an "alkenylene radical" is an unsaturated hydrocarbon-based divalent radical as defined previously, which may contain from 1 to 4 conjugated or unconjugated —C=C— double bonds; the alkenylene group particularly contains 1 or 2 unsaturated groups;
- the expression "optionally substituted" attributed to the alkyl radical means that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle, optionally comprising another heteroatom identical to or different from nitrogen; v) or a quaternary ammonium group —$N^+R'R''R'''$, $M^-$ for which R', R" and R'", which may be identical or different, represent a hydrogen atom or a $C_1$-$C_4$ alkyl group, or else —$N^+R'R''R'''$ forms a heteroaryl such as imidazolium optionally substituted with a $C_1$-$C_4$ alkyl group, and $M^-$ represents the counterion of the corresponding organic acid, inorganic acid or halide;
- an "alkoxy radical" is an alkyl-oxy radical for which the alkyl radical is a linear or branched $C_1$-$C_{16}$ and preferentially $C_1$-$C_8$ hydrocarbon-based radical;
- when the alkoxy group is optionally substituted, this implies that the alkyl group is optionally substituted as defined hereinabove;
- the expression "at least one" is equivalent to "one or more"; and
- the expression "inclusive" for a range of concentrations means that the limits of the range are included in the defined range.

It should be noted that, in the text hereinbelow, unless otherwise indicated, the limits of a range of values are included in that range.

Compound of Formula (I)

One subject of the invention is therefore a para-aminophenol compound of formula (I) below, the addition salts thereof with an acid and the solvates thereof:

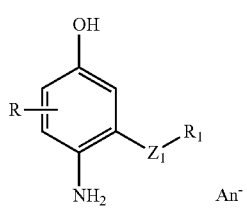

(I)

in which:
R represents a hydrogen or halogen atom; a $C_1$-$C_4$ alkyl radical; a carboxyl radical or a $(C_1$-$C_4)$alkoxycarbonyl radical;

Z1 is an oxygen atom or a group NR2;

R2 is a hydrogen atom or a linear or branched $C_1$-$C_4$ alkyl radical, a benzyl radical or an acetyl radical;

R1 is a saturated, linear or branched $C_1$-$C_{10}$ alkyl radical, which is substituted with or interrupted by a cationic radical, optionally interrupted by one or more oxygen atoms and/or by one or more groups NR2, optionally substituted with one or more radicals chosen from hydroxyl, alkoxy or $C_1$-$C_4$ hydroxyalkyl radicals;

or

R1 is a saturated, unsaturated or aromatic cationic 5- to 8-membered heterocycle optionally substituted with one or more radicals chosen from $C_1$-$C_4$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido or $C_1$-$C_4$ hydroxyalkyl radicals;

and when Z1 represents NR2 then

R1 and R2 may form, together with the nitrogen atom to which they are attached, a saturated or unsaturated cationic 5- to 8-membered heterocycle optionally substituted with one or more radicals chosen from $C_1$-$C_{10}$ alkyl radicals and hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals, it being possible for this heterocycle to contain one or more heteroatoms chosen from N or O, preferably N;

or

R1 and R2 may form, together with the nitrogen atom to which they are attached, a saturated or unsaturated non-cationic 5- to 8-membered heterocycle substituted with a cationic radical and optionally substituted with one or more radicals chosen from $C_1$-$C_{10}$ alkyl radicals and hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;

$An^-$ represents an anion or a mixture of anions which are organic or inorganic and are cosmetically acceptable.

The electroneutrality of the compounds of formula (I) is ensured by an anion or a mixture of anions, labelled $An^-$, which are organic or inorganic and are cosmetically acceptable.

$An^-$ represents an anion or a mixture of anions chosen, for example, from a halide such as chloride, bromide, fluoride or iodide; a hydroxide; a sulfate; a hydrogen sulfate; an alkylsulfate in which the linear or branched alkyl part is $C_1$-$C_6$, such as the methylsulfate or ethylsulfate ion; carbonates and hydrogen carbonates; salts of carboxylic acids, such as formate, acetate, citrate, tartrate and oxalate; alkyl sulfonates for which the linear or branched alkyl part is $C_1$-$C_6$, such as the methylsulfonate ion; arylsulfonates for which the aryl part, preferably phenyl, is optionally substituted with one or more $C_1$-$C_4$ alkyl radicals, for instance 4-toluoylsulfonate; and alkylsulfonyls such as mesylate.

The compounds of general formula (I) may be in free form or in the form of salts, such as addition salts with an inorganic acid preferably chosen from hydrochloric acid, hydrobromic acid, sulfuric acid and phosphoric acid or with an organic acid such as, for example, citric acid, succinic acid, tartaric acid, lactic acid, 4-toluoylsulfonic acid, benzenesulfonic acid, acetic acid, para-toluenesulfonic acid, formic acid and methanesulfonic acid.

The compounds of general formula (I) may also be in the form of solvates, for example a hydrate or a solvate of a linear or branched alcohol such as ethanol or isopropanol.

In the context of the invention, the expression "cationic radical present in the compound of formula (I)" is understood to mean any linear or branched or heterocyclic radical comprising a quaternary ammonium, this quaternary ammonium being of the type —N$^+$RaRbRc, Ra, Rb and Rc, which may be identical or different, representing a $C_1$-$C_6$ alkyl radical which may be substituted with a hydroxyl. Ra and Rb may together form a 5- to 8-membered heterocycle, in which case the radical Rc is a $C_1$-$C_6$ alkyl radical which may be substituted with a hydroxyl.

As examples of cationic radicals, mention may be made of trimethylammonium, triethylammonium, dimethylethylammonium, diethylmethylammonium, diisopropylmethylammonium, diethylpropylammonium, hydroxyethyldiethylammonium, di-β-hydroxyethylmethylammonium, tri-β-hydroxyethylammonium, piperidinium, N-methylpiperidinium, pyrrolidinium, N-methylpyrrolidinium, morpholinium, N-methylmorpholinium, imidazolium, hydroxyethylimidazolium, methylimidazolium, piperazinium and N-methylpiperazinium radicals and mixtures thereof.

The expression "cationic heterocycle" is understood to mean a 5- to 8-membered heterocycle in which one of the ring members is a quaternary ammonium. Examples of a cationic heterocycle that may be mentioned include imidazolium, pyridinium, piperidinium, piperazinium, pyrrolidinium, morpholinium, pyrimidinium, thiazolium, benzimidazolium, benzothiazolium, oxazolium, benzotriazolium, pyrazolium, triazolium and benzoxazolium radicals.

These cationic heterocycles are optionally substituted by one or more identical or different radicals chosen from ($C_1$-$C_4$)alkyl and hydroxy($C_1$-$C_4$)alkyl radicals.

According to one preferred embodiment, in formula (I):
R represents a hydrogen atom or a $C_1$-$C_4$ alkyl radical, more preferably still, R represents a hydrogen atom;
Z1 represents an oxygen atom or a group NR2, R2 being chosen from a hydrogen atom or a $C_1$-$C_2$ alkyl radical, and more preferably R2 is chosen from H or $CH_3$;
R1 is a linear or branched $C_1$-$C_8$ alkyl radical, which is substituted with or interrupted by a cationic radical, optionally interrupted by one or more oxygen atoms and/or by one or more groups NR2, optionally substituted with a hydroxyl radical, said cationic radical being optionally substituted with one or more radicals chosen from $C_1$-$C_4$ alkyl or $C_1$-$C_4$ alkoxy radicals;
or
R1 is a saturated, unsaturated or aromatic cationic 5- to 8-membered heterocycle optionally substituted with one or more radicals chosen from $C_1$-$C_4$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido or $C_1$-$C_4$ hydroxyalkyl radicals;
and when Z1 represents NR2 then
R1 and R2 may form, together with the nitrogen atom to which they are attached, a saturated or unsaturated cationic 5- to 8-membered heterocycle optionally substituted with one or more radicals chosen from $C_1$-$C_{10}$ alkyl radicals and hydroxyl, $C_1$-$C_4$ alkoxy, amino, ($C_1$-$C_4$)alkylamino, di($C_1$-$C_4$)alkylamino, ($C_1$-$C_4$)alkylcarbonyl, amido and $C_1$-$C_4$ hydroxyalkyl radicals, it being possible for this heterocycle to contain one or more heteroatoms chosen from N or O, preferably N;
or
R1 and R2 may form, together with the nitrogen atom to which they are attached, a saturated or unsaturated noncationic 5- to 8-membered heterocycle substituted with a cationic radical and optionally substituted with one or more radicals chosen from $C_1$-$C_{10}$ alkyl radicals and hydroxyl, $C_1$-$C_4$ alkoxy, amino, ($C_1$-$C_4$)alkylamino, di($C_1$-$C_4$)alkylamino, ($C_1$-$C_4$)alkylcarbonyl, amido and $C_1$-$C_4$ hydroxyalkyl radicals.

Preferably, the cationic radical is chosen from trimethylammonium, triethylammonium, dimethylethylammonium, diethylmethylammonium, diisopropylmethylammonium, hydroxyethyldiethylammonium, imidazolium, pyridinium, piperazinium, pyrrolidinium, morpholinium, pyrimidinium, thiazolium, benzimidazolium and piperidinium radicals and mixtures thereof.

More preferably still, the cationic radicals are chosen from trimethylammonium, imidazolium, piperazinium, pyrrolidinium, piperidinium and morpholinium radicals and mixtures thereof.

According to a first preferred variant of the invention, R denotes a hydrogen atom, Z1 denotes an oxygen atom or the group NH or $NCH_3$ and R1 represents a saturated, linear $C_2$-$C_8$ alkyl radical, which is optionally interrupted by an oxygen atom or a group NH, optionally substituted with a hydroxyl radical, and substituted with a cationic radical chosen from trimethylammonium, imidazolium, piperazinium, pyrrolidinium, piperidinium and morpholinium radicals.

According to a second preferred variant of the invention, R denotes a hydrogen atom, Z1 is a group NR2 and R1 and R2 form, together with the nitrogen atom to which they are attached, a piperazinium, pyrrolidinium, piperidinium or morpholinium radical substituted with one or more identical or different radicals chosen from $C_1$-$C_4$ hydroxyalkyl and $C_1$-$C_4$ alkyl radicals, preferably a piperazinium ring substituted with one or more identical or different radicals chosen from $C_1$-$C_4$ hydroxyalkyl and $C_1$-$C_4$ alkyl radicals.

According to a third preferred variant of the invention, R denotes a hydrogen atom, Z1 is a group NR2 and R1 and R2 form, together with the nitrogen atom to which they are attached, a saturated or unsaturated noncationic 5- to 8-membered heterocycle substituted with a cationic radical preferably chosen from trimethylammonium, diethylmethylammonium, imidazolium, piperazinium, piperidinium, pyrrolidinium and morpholinium radicals. According to this variant and more preferably still, the noncationic heterocycle is chosen from pyrrolidine, piperidine and morpholine, this ring being substituted with a cationic radical chosen from trimethylammonium and diethylmethylammonium radicals. According to this variant and particularly preferably, the noncationic heterocycle is chosen from pyrrolidine and piperidine, this ring being substituted with a cationic radical chosen from trimethylammonium and diethylmethylammonium radicals, preferably the trimethylammonium radical.

The preferred compounds of formula (I) are the following:

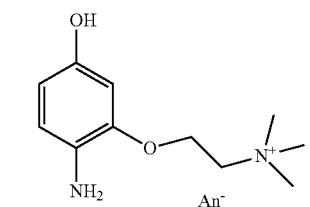

2-(2-amino-5-hydroxyphenoxy)-N,N,N-trimethylethanaminium, An⁻

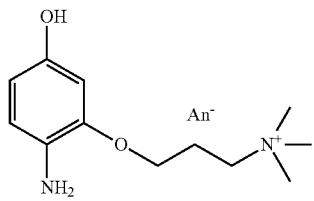

3-(2-amino-5-hydroxyphenoxy)-N,N,N-trimethylpropan-1-aminium, An⁻

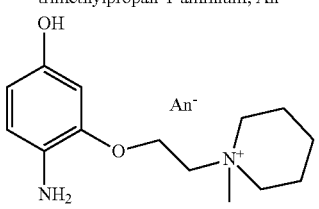

1-[2-(2-amino-5-hydroxyphenoxy)ethyl]-1-methylpiperidinium, An⁻

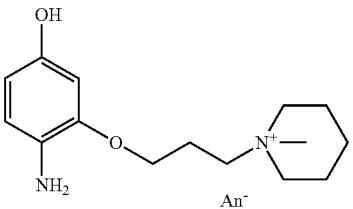

1-[3-(2-amino-5-hydroxyphenoxy)propyl]-1-methylpiperidinium, An⁻

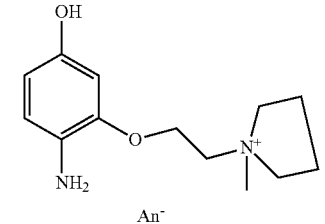

1-[2-(2-amino-5-hydroxyphenoxy)ethyl]-1-methylpyrrolidinium, An⁻

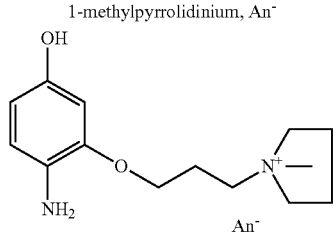

1-[3-(2-amino-5-hydroxyphenoxy)propyl]-1-methylpyrrolidinium, An⁻

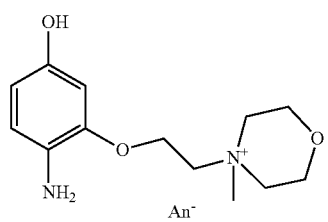

4-[2-(2-amino-5-hydroxyphenoxy)ethyl]-4-methylmorpholin-4-ium, An⁻

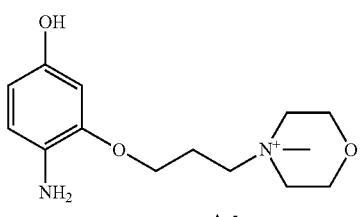

4-[3-(2-amino-5-hydroxyphenoxy)propyl]-4-methylmorpholin-4-ium, An⁻

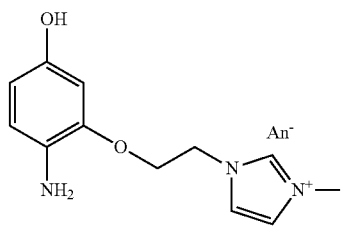

1-[2-(2-amino-5-hydroxyphenoxy)ethyl]-3-methyl-1H-imidazol-3-ium, An⁻

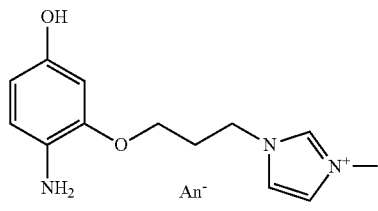

1-[3-(2-amino-5-hydroxyphenoxy)propyl]-3-methyl-1H-imidazol-3-ium, An⁻

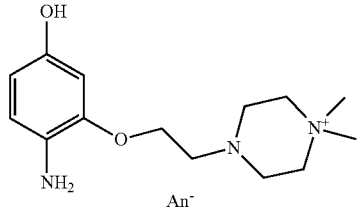

4-[2-(2-amino-5-hydroxyphenoxy)ethyl]-1,1-dimethylpiperazin-1-ium, An⁻

-continued

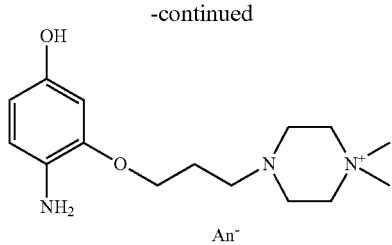

4-[3-(2-amino-5-hydroxyphenoxy)propyl]-
1,1-dimethylpiperazin-1-ium, An⁻

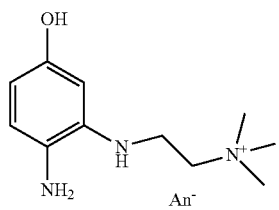

2-[(2-amino-5-hydroxyphenyl)amino]-
N,N,N-trimethylethanaminium, An⁻

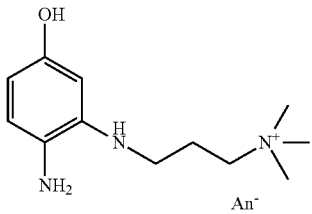

3-[(2-amino-5-hydroxyphenyl)amino]-
N,N,N-trimethylpropan-1-aminium, An⁻

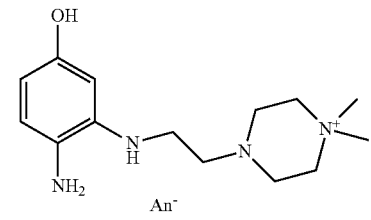

4-{2-[(2-amino-5-hydroxyphenyl)amino]ethyl}-1,1-
dimethylpiperazin-1-ium, An⁻

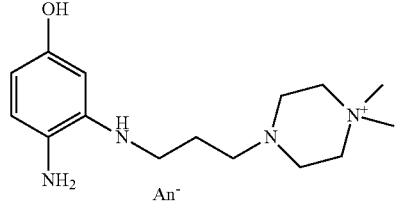

4-{3-[(2-amino-5-hydroxyphenyl)amino]propyl}-1,1-
dimethylpiperazin-1-ium, An⁻

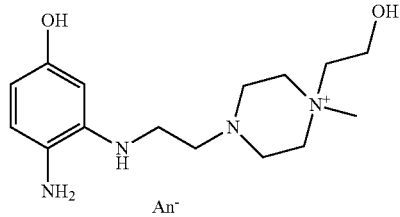

4-{2-[(2-amino-5-hydroxyphenyl)amino]ethyl}-1-(2-
hydroxyethyl)-1-methylpiperazin-1-ium, An⁻

-continued

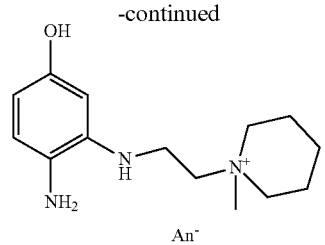

1-{2-[(2-amino-5-hydroxyphenyl)amino]ethyl}-
1-methylpiperidinium, An⁻

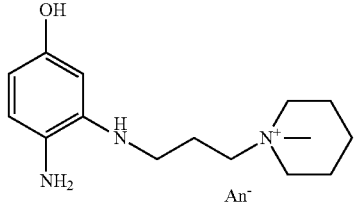

1-{3-[(2-amino-5-hydroxyphenyl)amino]propyl}-
1-methylpiperidinium, An⁻

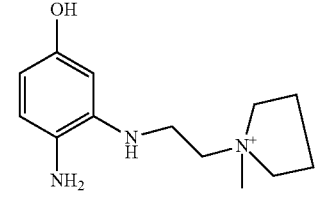

1-{2-[(2-amino-5-hydroxyphenyl)amino]ethyl}-
1-methylpyrrolidinium, An⁻

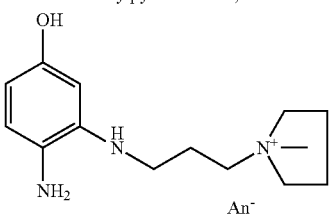

1-{3-[(2-amino-5-hydroxyphenyl)amino]propyl}-
1-methylpyrrolidinium, An⁻

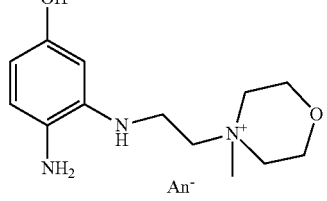

4-{2-[(2-amino-5-hydroxyphenyl)amino]ethyl}-
4-methylmorpholin-4-ium, An⁻

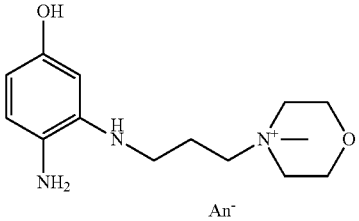

4-{3-[(2-amino-5-hydroxyphenyl)amino]propyl}-
4-methylmorpholin-4-ium, An⁻

-continued

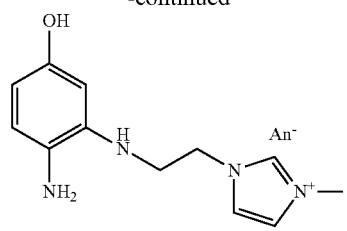

1-{2-[(2-amino-5-hydroxyphenyl)amino]ethyl}-
3-methyl-1H-imidazol-3-ium, An⁻

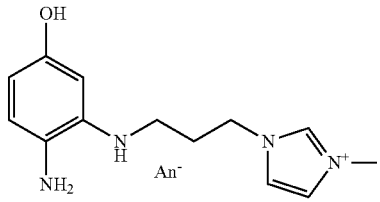

1-{3-[(2-amino-5-hydroxphenyl)amino]propyl}-
3-methyl-1H-imidazol-3-ium, An⁻

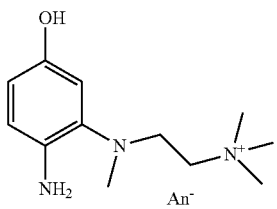

2-[(2-amino-5-hydroxyphenyl)(methyl)amino]-
N,N,N-trimethylethanaminium, An⁻

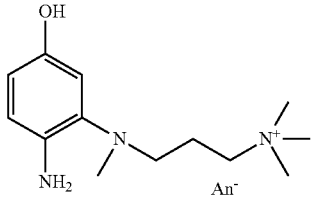

3-[(2-amino-5-hydroxyphenyl)(methyl)amino]-
N,N,N-trimethylpropan-1-aminium, An⁻

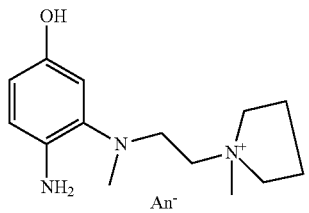

1-{2-[(2-amino-5-hydroxphenyl)(methyl)amino]ethyl}-
1-methylpyrrolidinium, An⁻

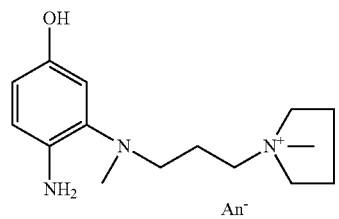

1-{3-[(2-amino-5-hydroxyphenyl)(methyl)amino]propyl}-
1-methylpyrrolidinium, An⁻

-continued

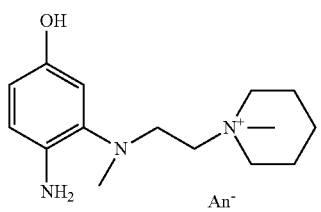

1-{2-[(2-amino-5-hydroxyphenyl)(methyl)amino]ethyl}-
1-methylpiperidinium, An⁻

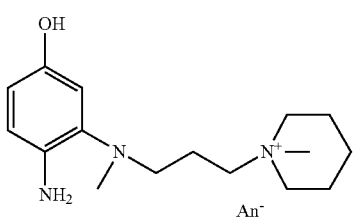

4-{3-[(2-amino-5-hydroxyphenyl)(methyl)amino]propyl}-
1-methylpiperidinium, An⁻

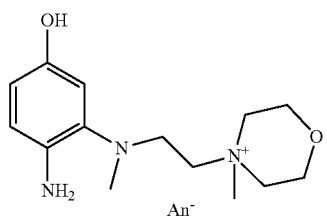

4-{2-[(2-amino-5-hydroxyphenyl)(methyl)amino]ethyl}-
4-methylmorpholin-4-ium, An⁻

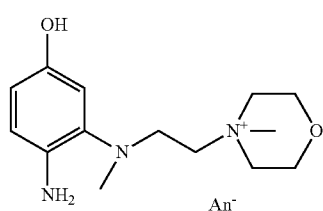

4-{3-[(2-amino-5-hydroxyphenyl)(methyl)amino]propyl}-
4-methylmorpholin-4-ium, An⁻

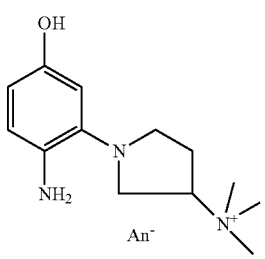

1-(2-amino-5-hydroxyphenyl)-
N,N,N-trimethylpyrrolidin-3-aminium, An⁻

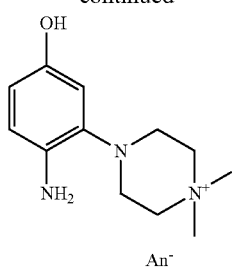

4-(2-amino-5-hydroxyphenyl)-
1,1-dimethylpiperazin-1-ium, An⁻

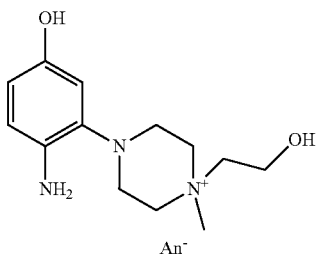

4-(2-amino-5-hydroxyphenyl)-1-(2-
hydroxyethyl)-1-methylpiperazin-1-ium, An⁻

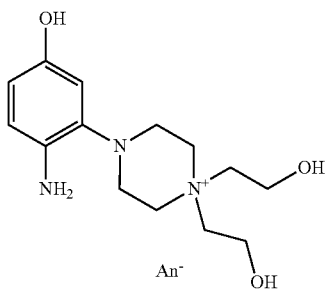

4-(2-amino-5-hydroxyphenyl)-1,1-bis(2-
hydroxyethyl)piperazin-1-ium, An⁻

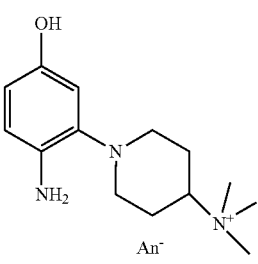

1-(2-amino-5-hydroxyphenyl)-N,N,N-
trimethylpiperidin-4-aminium, An⁻

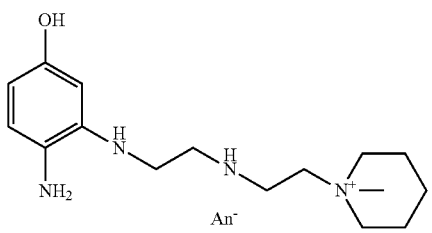

1-[2-({2-[(2-amino-5-
hydroxyphenyl)amino]ethyl}amino)ethyl]-
1-methylpiperidinium, An⁻

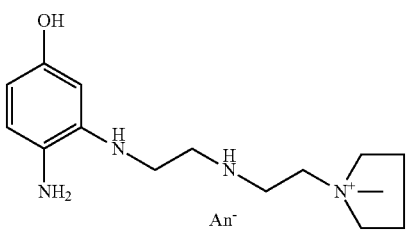

1-[2-({2-[(2-amino-5-
hydroxyphenyl)amino]ethyl}amino)ethyl]-
1-methylpyrrolidinium, An⁻

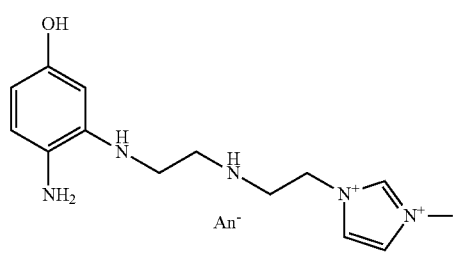

1-[2-({2-[(2-amino-5-
hydroxyphenyl)amino]ethyl}amino)ethyl]-
3-methyl-1H-imidazol-3-ium, An⁻

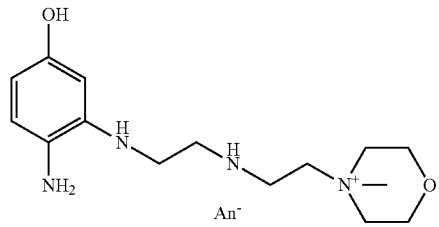

4-[2-({2-[(2-amino-5-
hydroxyphenyl)amino]ethyl}amino)ethyl]-
4-methylmorpholin-4-ium, An⁻

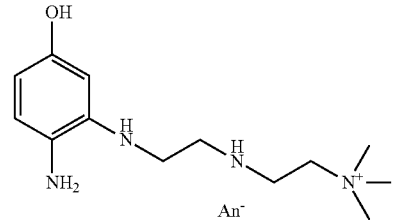

2-({2-[(2-amino-5-
hydroxyphenyl)amino]ethyl}amino)-
N,N,N-trimethylethanaminium, An⁻

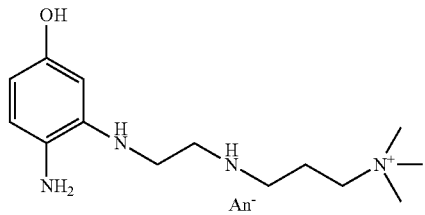

3-({2-[(2-amino-5-
hydroxyphenyl)amino]ethyl}amino)-
N,N,N-trimethylpropan-1-aminium, An⁻

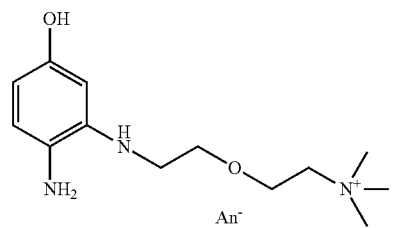

2-{2-[(2-amino-5-hydroxyphenyl)amino]ethoxy}-N,N,N-trimethylethanaminium, An⁻

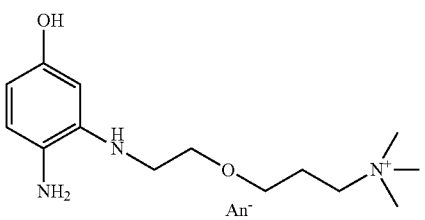

3-{2-[(2-amino-5-hydroxyphenyl)amino]ethoxy}-N,N,N-trimethylpropan-1-aminium, An⁻

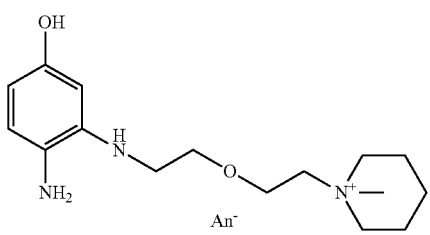

1-(2-{2-[(2-amino-5-hydroxyphenyl)amino]ethoxy}ethyl)-1-methylpiperidinium, An⁻

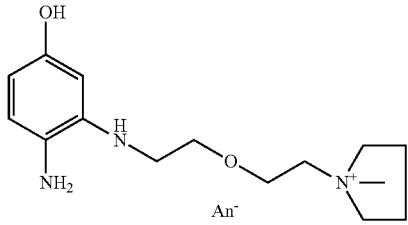

1-(2-{2-[(2-amino-5-hydroxyphenyl)amino]ethoxy}ethyl)-1-methylpyrrolidinium, An⁻

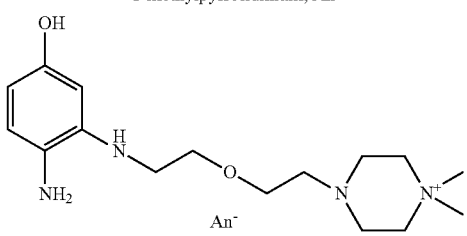

4-(2-{2-[(2-amino-5-hydroxyphenyl)amino]ethoxy}ethyl)-1,1-dimethylpiperazin-1-ium, An⁻

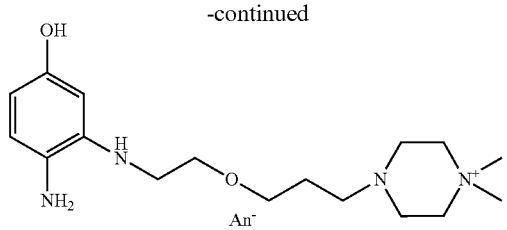

4-(3-{2-[(2-amino-5-hydroxyphenyl)amino]ethoxy}propyl)-1,1-dimethylpiperazin-1-ium, An⁻

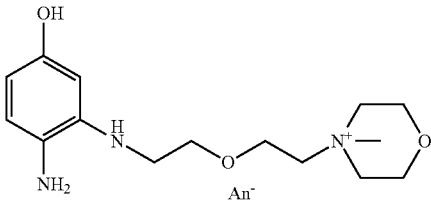

4-(2{2-[(2-amino-5-hydroxyphenyl)amino]ethoxy}ethyl)-4-methylmorpholin-4-ium, An⁻

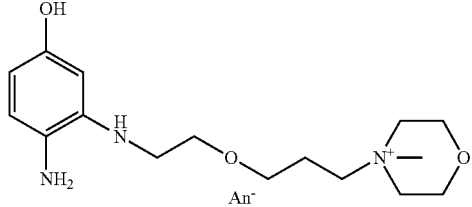

4-(3-{2-[(2-amino-5-hydroxyphenyl)amino]ethoxy}propyl)-4-methylmorpholin-4-ium, An⁻ and also the salts and/or solvates or isomers thereof, An⁻ having the same meaning as before,
and mixtures thereof.

According to one particularly preferred embodiment, the para-aminophenol compound is chosen from the compounds of formula (I) below, the addition salts thereof and the solvates thereof:

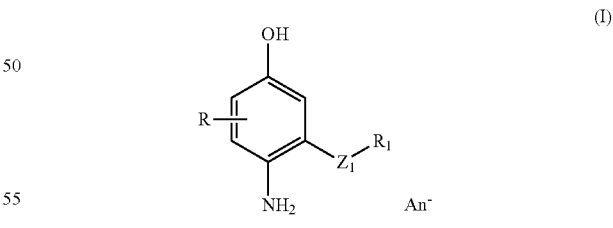

(I)

in which:
R represents a hydrogen atom;
Z1 is a group NR2, preferably NH or NCH₃; and
R1 and R2 form, together with the nitrogen atom to which they are attached, a piperazinium, pyrrolidinium, piperidinium or morpholinium radical, preferably a piperazinium radical, substituted with one or more identical or different radicals chosen from $C_1$-$C_4$ hydroxyalkyl and $C_1$-$C_4$ alkyl radicals, preferably a piperazinium ring substituted with one or more identical or different radicals chosen from $C_1$-$C_4$ hydroxyalkyl and $C_1$-$C_4$ alkyl radicals, preferably $C_1$-$C_4$ alkyl radicals and better still a methyl radical.

An⁻ represents an anion or a mixture of anions which are organic or inorganic and are cosmetically acceptable.

More preferably, the para-aminophenol compound of formula (I) is chosen from 4-(2-amino-5-hydroxyphenyl)-1,1-dimethylpiperazin-1-ium, salts thereof and solvates thereof.

Dye Composition

Another subject of the invention is a composition for dyeing keratin fibres comprising, in a suitable medium, at least one compound of formula (I) as defined above.

The compound of formula (I) may be present in the composition in an amount of between 0.001% and 10%, preferably between 0.005% and 6%, by weight approximately of the total weight of the dye composition.

Couplers

The dye composition according to the invention may contain and preferably contains one or more couplers that are conventionally used for dyeing keratin fibres. Among these couplers, mention may be made especially of meta-phenylenediamines, meta-aminophenols, meta-diphenols, naphthalene couplers and heterocyclic couplers, and the addition salts thereof.

Examples of a coupler that may be mentioned include 2-methyl-5-aminophenol, 5-N-(β-hydroxyethyl)amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methyl-naphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxy-pyridine, 2,6-dihydroxy-3-4-dimethylpyridine, 3-amino-2-methylamino-6-methoxypyridine, 1-N-(β-hydroxyethyl)amino-3,4-methylenedioxybenzene, 2,6-bis(β-hydroxyethylamino)toluene and 3-methyl-1-phenyl-5-pyrazolone and the addition salts thereof with an acid.

In the dye composition of the present invention, the coupler(s), if it (they) is (are) present, generally represent(s) an amount of between 0.001% and 10% by weight, preferably between 0.005% and 6% by weight approximately of the total weight of the composition.

Additional Oxidation Bases

The dye composition of the invention may optionally comprise one or more additional oxidation bases conventionally used for dyeing keratin fibres, other than the compounds of formula (I).

By way of example, these additional oxidation bases are chosen from para-phenylenediamines, other than the bases of formula (I), bis(phenyl)alkylenediamines, para-aminophenols, bis-para-aminophenols, ortho-aminophenols, heterocyclic bases, and the addition salts thereof.

Among the para-phenylenediamines, mention may be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis((3-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-(β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bisphenylalkylenediamines, mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols, mention may be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 1-hydroxy-4-methylaminobenzene and 2,2'-methylenebis(4-aminophenol), and the addition salts thereof with an acid.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid.

Among the heterocyclic bases, mention may be made, by way of example, of pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made of the compounds described, for example, in patents DE 2 359 399; JP 88-169 571; JP 05-163124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7diamine, pyrazolo[1,5-a]pyrimidine-3,5-diamine, 2,7-dimethylpyrazolo[1,5a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5a]pyrimidine-3,7-diamine, 2,5,-N7,N7-tetramethylpyrazolo[1,5-a]pyrimidine-3,7diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives, mention may be made of the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-1-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

In general, the addition salts of the additional oxidation bases and of the couplers that can be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

The dye composition in accordance with the invention may also contain one or more direct dyes that may in particular be chosen from nitrobenzene dyes, azo direct dyes and methine direct dyes. These direct dyes may be of nonionic, anionic or cationic nature.

The medium that is suitable for dyeing, also known as the dye support, generally comprises water or a mixture of water and of one or more solvents, for instance $C_1$-$C_4$ lower alkanols such as ethanol and isopropanol, polyols, for instance propylene glycol, dipropylene glycol or glycerol, and polyol ethers, for instance dipropylene glycol monomethyl ether.

The solvent(s) is (are) generally present in proportions that may be between 1% and 40% by weight approximately and more preferably between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or alkalinizing agents customarily used in the dyeing of keratin fibres, or alternatively using standard buffer systems.

Among the acidifying agents, mention made be made, by way of example, of inorganic or organic acids, for instance hydrochloric acid, orthophosphoric acid, sulfuric acid, carboxylic acids, for instance acetic acid, tartaric acid, citric acid and lactic acid, and sulfonic acids.

Among the alkalinizing agents, mention made be made, by way of example, of aqueous ammonia, alkali metal carbonates, alkanolamines, such as mono-, di- and triethanolamines and derivatives thereof, sodium hydroxide, potassium hydroxide and the compounds of formula (III) below:

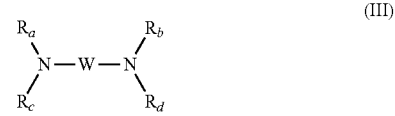

(III)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The composition according to the invention may comprise one or more oxidizing agents.

The oxidizing agents are those conventionally used for the oxidation dyeing of keratin fibres, for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The dye composition with or without oxidizing agent according to the invention may be in various forms, such as in the form of liquids, creams or gels, or in any other form that is suitable for dyeing keratin fibres, and especially human hair.

It may result from the mixing, at the time of use, of several compositions.

In particular, it results from the mixing of at least two compositions, one comprising one or more oxidation bases chosen from the compounds of formula (I) or the addition salts thereof with an acid, optionally one or more additional oxidation bases other than the compounds of formula (I) or salts thereof, and optionally one or more couplers, and a second composition comprising one or more oxidizing agents as described above.

The composition of the invention is thus applied to the hair for the dyeing of keratin fibres, either as is or in the presence of one or more oxidizing agents for the dyeing of keratin fibres.

The process of the present invention is a process in which the composition according to the present invention as defined previously is applied to the fibres, either alone or in the presence of an oxidizing agent, for a time that is sufficient to develop the desired colouring. The colour may be developed at acidic, neutral or alkaline pH, and the oxidizing agent may be added to the composition of the invention just at the time of use, or it may be used starting from an oxidizing composition which comprises it and which is applied simultaneously with or sequentially to the composition of the invention.

In one particular embodiment, the composition devoid of oxidizing agent according to the present invention is mixed, preferably at the time of use, with a composition containing, in a medium appropriate for dyeing, one or more oxidizing agents, these oxidizing agents being present in an amount sufficient to develop a colouring. The mixture obtained is then applied to the keratin fibres. After a leave-in time of approximately 3 to 50 minutes, preferably approximately 5 to 30 minutes, the keratin fibres are rinsed, washed with shampoo, rinsed again and then dried.

The oxidizing agents are those indicated above.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably varies between 3 and 12 approximately and more preferably still between 5 and 11. It may be adjusted to the desired value by means of acidifying or alkalinizing agents customarily used in the dyeing of keratin fibres and as defined above.

The ready-to-use composition which is ultimately applied to the keratin fibres may be in a variety of forms, such as in the form of liquids, creams or gels or any other form appropriate for carrying out dyeing of keratin fibres, and in particular of human hair.

Another subject of the invention is a dyeing "kit" or multi-compartment device in which a first compartment contains the dye composition devoid of oxidizing agent of the present invention defined above, comprising one or more oxidation bases chosen from the compound of formula (I) or the addition salts thereof with an acid, and a second compartment contains one or more oxidizing agents.

These devices may be equipped with a means for dispensing the desired mixture on the hair, such as the devices described in patent FR-2 586 913 in the name of the Applicant.

Preparation of the Compound of Formula (I)

According to a particular embodiment, the synthesis of the compounds of formula (I) may be carried out according to the following scheme:

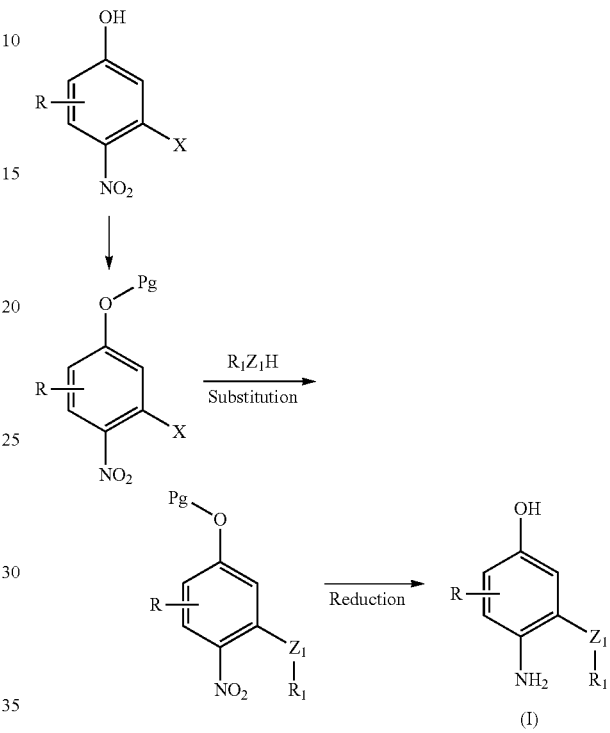

X = halogen or SO₂R
Pg: reduction-cleavable protecting group such as for example benzyl, Boc The substitution reaction is performed in a dipolar solvent such as acetonitrile, THF or in DMF or NMP, or in an alcohol such as ethanol for example, in the presence of a base such as triethylamine, ethyldiisopropylamine, sodium hydroxide or potassium hydroxide, for example, and one or more R1Z1H equivalents for 1 to 24 hours at a temperature from 20° C. to the reflux temperature of the solvent.

According to another embodiment, when $R_1$ represents a $C_1$-$C_{10}$ alkyl radical substituted with a cationic radical, said alkyl radical being interrupted by one or more heteroatoms chosen from NR2 or O, then the method of synthesis used may be the following:

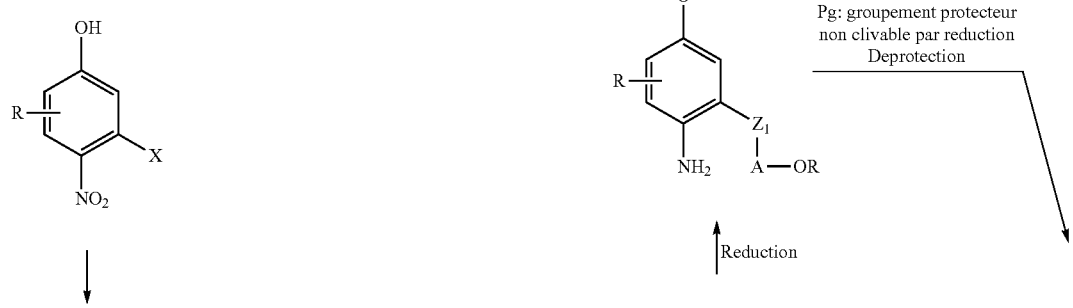

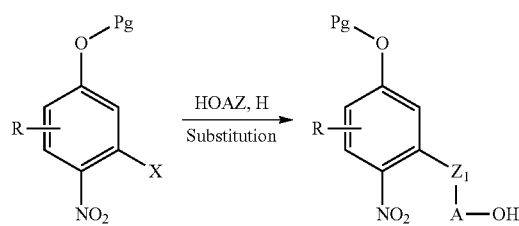 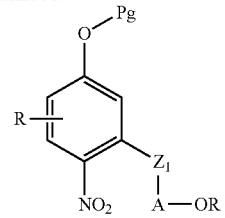 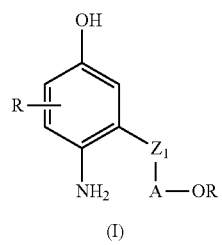

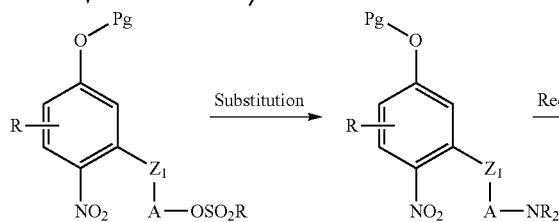

X = halogen or SO$_2$R

A = alkyl

Pg: reduction-cleavable protecting group such as for example benzyl, Boc

The substitution reaction is performed in a dipolar solvent such as acetonitrile, THF or in DMF or NMP, or in an alcohol such as ethanol for example, in the presence of a base such as triethylamine, ethyldiisopropylamine, sodium hydroxide or potassium hydroxide, for example, and one or more HOAZ1H equivalents for 1 to 24 hours at a temperature from 20° C. to the reflux temperature of the solvent.

The hydroxyl function thus introduced is then substituted with a halide in order to introduce a leaving group (for example mesyl or tosyl halide) in a solvent such as acetonitrile, THF or in an alcohol such as ethanol for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced during the preceding step is carried out by reaction with an amine R2NH or an alcohol ROH.

The reduction of the nitro group of these compounds is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The following synthesis scheme makes it possible, inter alia, to obtain compounds for which R1 is substituted with a cationic radical.

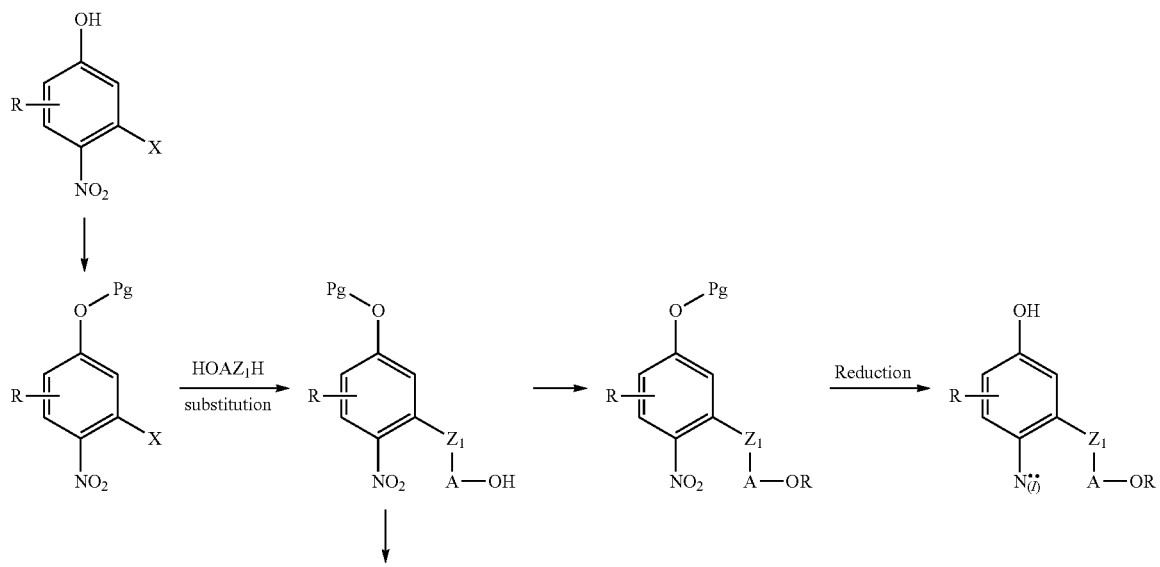

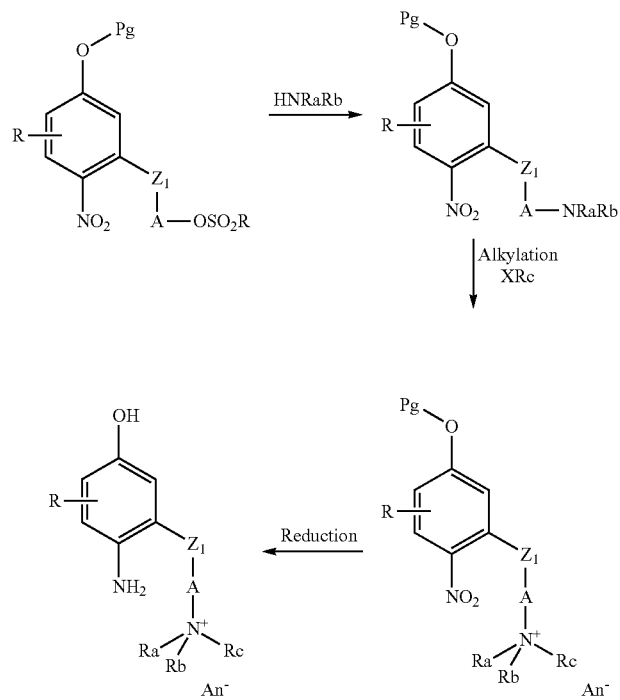

Pg: reduction-cleavable protecting group for example benzyl, Boc
X = halogen or SO₂R
A = alkyl The substitution reaction is performed in a dipolar solvent such as acetonitrile, THF or in DMF or NMP, or in an alcohol such as ethanol for example, in the presence of a base such as triethylamine, ethyldiisopropylamine, sodium hydroxide or potassium hydroxide, for example, and one or more HOAZ1H equivalents for 1 to 24 hours at a temperature from 20° C. to the reflux temperature of the solvent.

The hydroxyl function thus introduced is then substituted with a halide in order to introduce a leaving group (for example mesyl or tosyl halide) in a solvent such as acetonitrile, THF or in an alcohol such as ethanol for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced in the preceding step is performed either by reaction with an aromatic tertiary amine such as methylimidazole to lead directly to the cationic compounds, or by reaction with a particular primary or secondary amine HNRaRb, for instance N,N-dimethylethylenediamine or 2-piperidin-1-ylethanamine to lead to the compounds that are alkylated with at least one equivalent of alkyl halide or methyl sulfate in a solvent such as THF or acetonitrile or dioxane or ethyl acetate for 15 minutes to 24 hours at a temperature ranging from 15° C. to the reflux temperature of the solvent, to give the cationic nitro compounds.

The reduction of the nitro group of these compounds is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The examples that follow serve to illustrate the invention without, however, being limiting in nature.

EXAMPLES

Synthesis Examples

Example 1

Synthesis of 2-(2-amino-5-hydroxyphenoxy)-N,N,N-trimethylethanaminium chloride hydrochloride

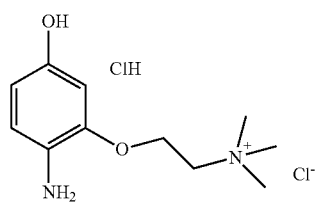

Synthesis of 2-[5-(benzyloxy)-2-nitrophenoxy]-N,N-dimethylethanamine

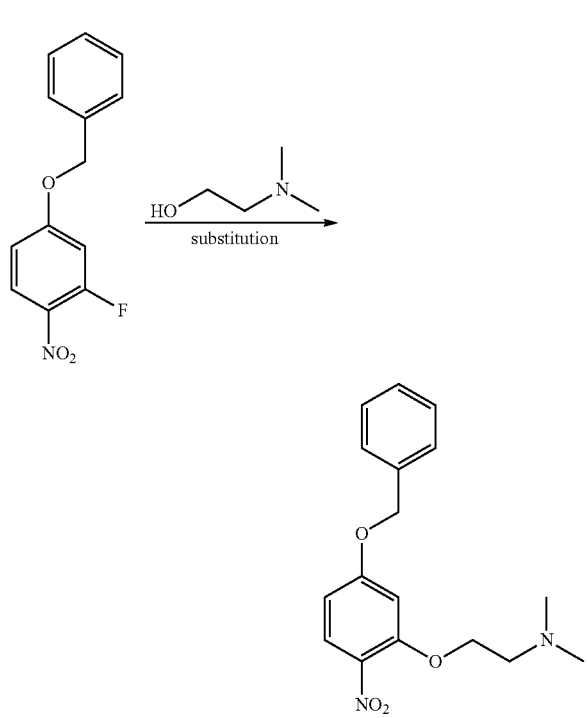

A 250 ml three-necked flask equipped with a thermometer, a condenser, a bubble counter and a dropping funnel, and with magnetic stirring, is charged with 50 ml of THF and 6.15 ml (60.67 mmol) of N,N-dimethylethanolamine and then 2.43 g (60.67 mmol) of 60% sodium hydride are introduced by spatula. Gas evolution is observed, and also a slight exothermicity (the temperature changes from 19° C. to 27° C.). The temperature is kept below 30° C. using an ice bath. The reaction medium then continues to be stirred at room temperature for 1 h.

The solution thus obtained is poured dropwise, with stirring, into a solution of 10 g (40.44 mmol) of 4-(benzyloxy)-2-fluoro-1-nitrobenzene in 120 ml of THF.

A slight exothermicity is observed during this pouring operation. The medium then continues to be stirred at room temperature for 3 h.

The solvent is evaporated using a rotary evaporator and the red oil obtained is then taken up in 250 ml of ethyl acetate and then the organic phase is washed with 3×120 ml of water before being dried over sodium sulfate.

After removal of the ethyl acetate, the isolated crude product is purified by chromatography on a silica column, eluent=MeOH/CH$_2$Cl$_2$. The expected product is isolated in the form of a red oil having a mass of 11.59 g, yield=90.6%.

Analysis by mass spectrometry confirms the structure of the expected compound. The quasi-molecular ions [M+H]$^+$ and [M+Na]$^+$ of the expected molecule are mainly detected, $C_{17}H_{20}N_2O_4$.

Synthesis of 2-[5-(benzyloxy)-2-nitrophenoxy]-N,N,N-trimethylethanaminium methyl sulfate

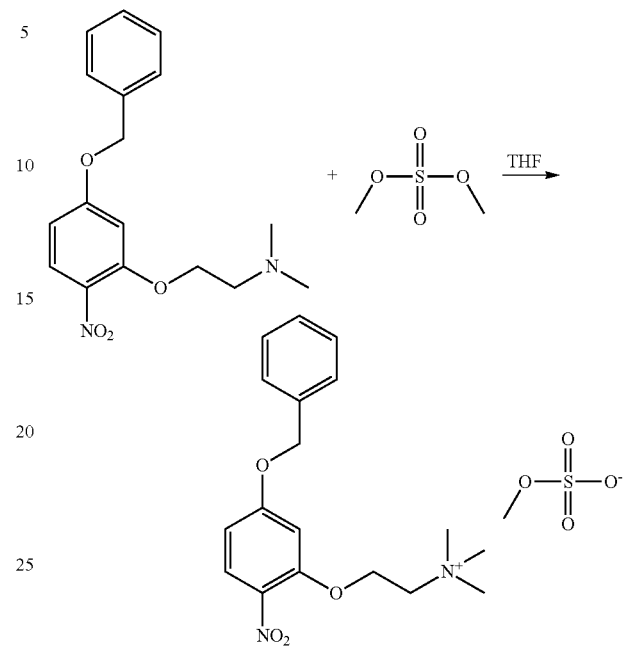

A 250 ml three-necked flask equipped with a thermometer, a condenser, a bubble counter and a dropping funnel, and with magnetic stirring, is charged successively with 70 ml of THF and 6 g (19 mmol) of 2-[5-(benzyloxy)-2-nitrophenoxy]-N,N-dimethylethanamine. Added dropwise to this solution are 1.9 ml (20 mmol) of dimethyl sulfate and the whole assembly continues to be stirred for 3 hours.

The yellow solid formed is filtered off, drained by suction, washed with THF and then dried under vacuum at 50° C. in the presence of a desiccant, to constant mass. 7.22 g (86% yield) of the expected compound are thus obtained in the form of a yellow solid.

Analysis by mass spectrometry confirms the structure of the expected compound. The quasi-molecular ions [M+H]$^+$, [M+Na]$^+$, [2M+Na]$^+$, [M–H]$^-$, [M+Cl]$^-$ of the expected molecule are mainly detected.

Synthesis of 2-(2-amino-5-hydroxyphenoxy)-N,N,N-trimethylethanaminium chloride hydrochloride

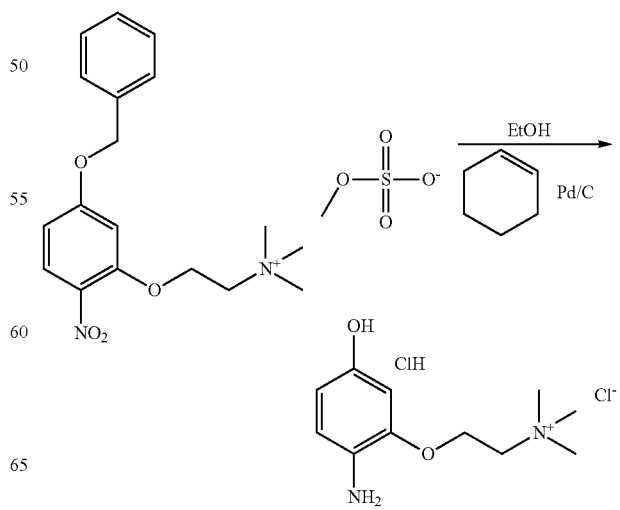

A 500 ml three-necked flask equipped with a thermometer, a condenser and a bubble counter, and with magnetic stirring, is charged successively with 100 ml of ethanol, 27.5 ml of cyclohexene and 3 g of 50% wet 5% palladium-on-charcoal. This medium is brought to reflux and a solution formed of 10 ml of water, 100 ml of ethanol and 6 g (13.56 mmol) of trimethylethanaminium methyl sulfate is added dropwise thereto. Once the addition is completed, the solution is left under reflux for 5 h.

After cooling under argon, the reaction medium is filtered under a stream of argon through a sintered glass funnel packed with Celite into a vacuum flask containing 30 ml of 6.0N hydrochloric acid in 2-propanol at 0° C.

In the absence of a precipitate, the filtrate is concentrated to around 30 ml then taken up in 200 ml of isopropanol and then concentrated again. The operation is repeated until a precipitate appears. The precipitate formed is then filtered on a sintered glass funnel in the presence of argon (highly hygroscopic product), washed with 50 ml of isopropanol then 3×50 ml of diisopropyl ether before being dried under vacuum at 40° C. in the presence of a desiccant until a constant weight is obtained.

Thus 3.53 g of a grey powder are obtained (yield=91.9%) corresponding to the expected product.

The NMR ($^1$H 400 MHz and $^{13}$C 100.61 MHz DMSO-$d_6$) and mass spectrometry analyses are in accordance with the expected structure. The expected cation $C_{11}H_{19}N_2O_2$ is mainly detected.

Example 2

Synthesis of 1-[2-(2-amino-5-hydroxyphenoxy) ethyl]-1-methylpiperidinium chloride hydrochloride

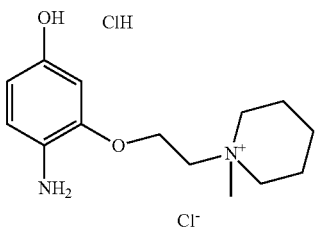 [SMILES: C[N+]1(CCOc2cc(O)ccc2N)CCCCC1 ; Cl ; [Cl-]]

Synthesis of 1-{2-[5-(benzyloxy)-2-nitrophenoxy] ethyl}piperidine

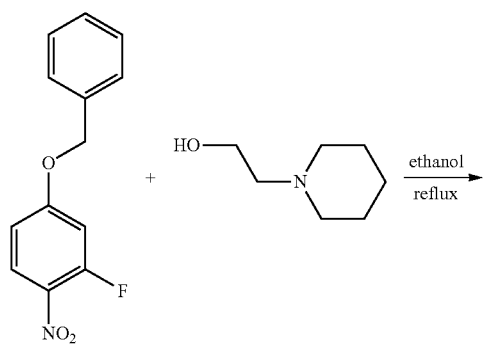

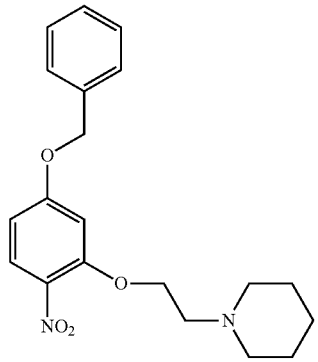

A 250 ml three-necked flask equipped with a thermometer, a condenser, a bubble counter and a dropping funnel, and with magnetic stirring, is charged with 120 ml of THF and 8.1 ml (60.67 mmol) of 1-piperidineethanol and then 2.43 g (60.67 mmol) of 60% sodium hydride are introduced by spatula.

Gas evolution is observed, and also a slight exothermicity. The temperature is kept below 30° C. using an ice bath. The solution formed (solution A) is then stirred at room temperature for 1 h.

This solution (A) is poured dropwise, with stirring, into a solution of 10 g (40.44 mmol) of 4-(benzyloxy)-2-fluoro-1-nitrobenzene in 120 ml of THF.

A slight exothermicity is observed during this pouring operation. The reaction medium then continues to be stirred at ambient temperature for 1 hour.

The solvent is evaporated using a rotary evaporator and the red oil obtained is taken up in 250 ml of ethyl acetate and then the organic phase is washed with 3×120 ml of water before being dried over sodium sulfate. After removal of the ethyl acetate, the isolated crude product is purified by chromatography on a silica column. The expected product is isolated in the form of a red oil (14.17 g, yield=98.3%).

Synthesis of 1-{2-[5-(benzyloxy)-2-nitrophenoxy] ethyl}-1-methylpiperidinium methyl sulfate

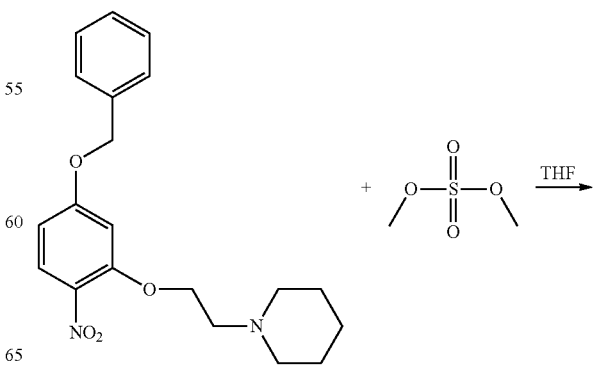

-continued

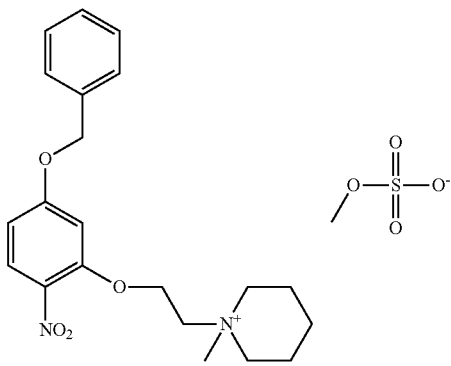

A 250 ml three-necked flask equipped with a thermometer, a condenser, a bubble counter and a dropping funnel, and with magnetic stirring, is charged successively with 100 ml of THF and 6 g (16.83 mmol) of 1-{2-[5-(benzyloxy)-2-nitrophenoxy]ethyl}piperidine.

Added dropwise to this solution are 1.7 ml (17.67 mmol) of dimethyl sulfate and the whole assembly continues to be stirred at room temperature for 3 hours. The yellow solid formed is filtered off on a sintered glass funnel, drained by suction, washed with THF and then dried under vacuum at 50° C. in the presence of a desiccant, to constant weight. 6.63 g (81.6% yield) of the expected compound are thus isolated in the form of a yellow solid.

Mass spectrometry analysis confirms the structure of the expected compound. The expected cation $[C_{21}H_{27}N_2O_4]^+$ is mainly detected.

Synthesis of 1-[2-(2-amino-5-hydroxyphenoxy) ethyl]-1-methylpiperidinium chloride hydrochloride

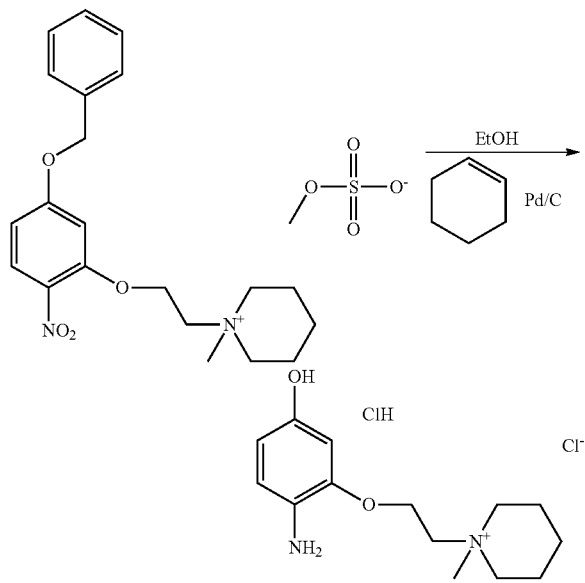

A 500 ml three-necked flask equipped with a thermometer, a condenser and a bubble counter, and with magnetic stirring, is charged successively with 100 ml of ethanol, 28.4 ml of cyclohexene and 2.5 g of 50% wet 5% palladium-on-charcoal. This medium is brought to reflux and then a solution of 5 ml of water, 25 ml of ethanol and 5 g (10.7 mmol) of 1-{2-[5-(benzyloxy)-2-nitrophenoxy]ethyl}-1-methylpiperidinium methyl sulfate is then added dropwise to the reaction medium. Once the addition is completed, the solution is left under reflux for 5 hours. After cooling under argon, the reaction medium is filtered under a stream of argon through a sintered glass funnel packed with Celite into a vacuum flask containing 25 ml of 6.0N hydrochloric acid in 2-propanol at 0° C.

In the absence of a precipitate, the filtrate is concentrated until around 30 ml is obtained, then taken up in 200 ml of isopropanol and then concentrated again. The operation is repeated until a precipitate appears. The precipitate formed is filtered on a sintered glass funnel in the presence of argon (highly hygroscopic product), washed with 50 ml of isopropanol then 3×50 ml of diisopropyl ether.

After drying under vacuum at 40° C., in the presence of a desiccant, to a constant weight, 2.86 g of a grey powder corresponding to the expected product are obtained. (Yield=71.3%).

Mass spectrometry analysis confirms the structure of the expected compound. The expected cation $[C_{14}H_{23}N_2O_2]^+$ is mainly detected.

Example 3

Synthesis of 4-[2-(2-amino-5-hydroxyphenoxy) ethyl]-4-methyl-morpholin-4-ium chloride hydrochloride

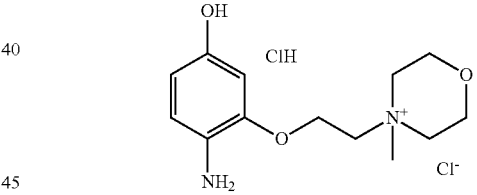

Synthesis of 4-{2-[5-(benzyloxy)-2-nitrophenoxy] ethyl}morpholine

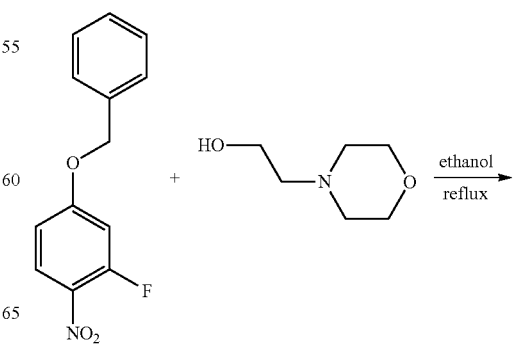

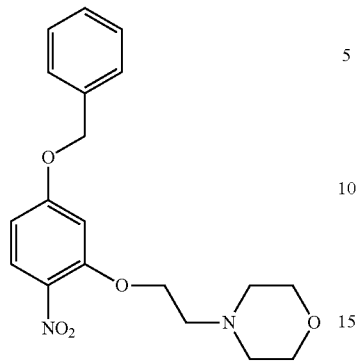

A 250 ml three-necked flask equipped with a thermometer, a condenser, a bubble counter and a dropping funnel, and with magnetic stirring, is charged with 120 ml of THF and 7.4 ml (60.67 mmol) of 2-(morpholin-4-yl)ethanol and then 2.43 g (60.67 mmol) of 60% sodium hydride are introduced by spatula.

Gas evolution is observed, and also a slight exothermicity (19° C. to 27° C.). The temperature is kept below 30° C. using an ice bath. The reaction medium is maintained at room temperature for 1 h.

The solution thus obtained is poured dropwise, with stirring, into a solution of 10 g (40.44 mmol) of 4-(benzyloxy)-2-fluoro-1-nitrobenzene in 120 ml of THF (slight exothermicity observed). The reaction medium is then maintained at room temperature for 1 hour.

The solvent is evaporated using a rotary evaporator and the residue is purified by chromatography on a silica column. The expected product is isolated in the form of a red oil having a mass of 14.38 g, yield=99.2%.

Analysis by mass spectrometry confirms the structure of the expected compound. The quasi-molecular ions $[M+H]^+$, $[M+Na]^+$, $[M+K]^+$, $[2M+Na]^+$, $[M+Cl]^-$ of the expected molecule $C_{19}H_{22}N_2O_5$ are mainly detected.

Synthesis of 4-{2-[5-(benzyloxy)-2-nitrophenoxy]ethyl}-4-methylmorpholin-4-ium methyl sulfate

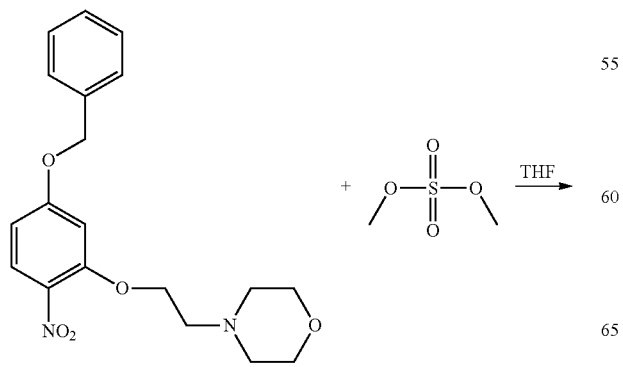

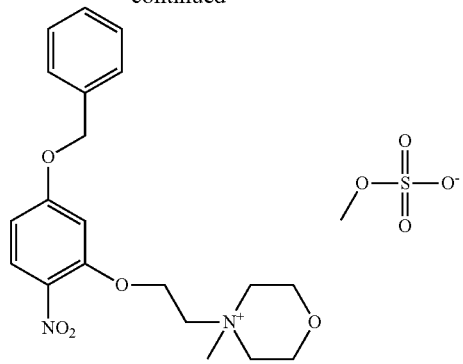

A 250 ml three-necked flask equipped with a thermometer, a condenser, a bubble counter and a dropping funnel, and with magnetic stirring, is charged successively with 70 ml of THF and 6 g (16.74 mmol) of 4-{2-[5-(benzyloxy)-2-nitrophenoxy]ethyl}morpholine.

Added dropwise to this solution are 1.7 ml (17.67 mmol) of dimethyl sulfate and the whole assembly continues to be stirred at room temperature for 3 hours. The yellow solid formed is filtered off on a sintered glass funnel, drained by suction, washed with THF and then dried under vacuum at 50° C. in the presence of a desiccant until a constant weight is obtained. 4.74 g (58.2% yield) of the expected compound are thus isolated in the form of a yellow solid.

Mass spectrometry analysis confirms the structure of the expected compound. The expected cation $[C_{20}H_{25}N_2O_5]^+$ is mainly detected.

Synthesis of 4-amino-3-[2-(morpholin-4-yl)ethoxy]phenol chloride hydrochloride

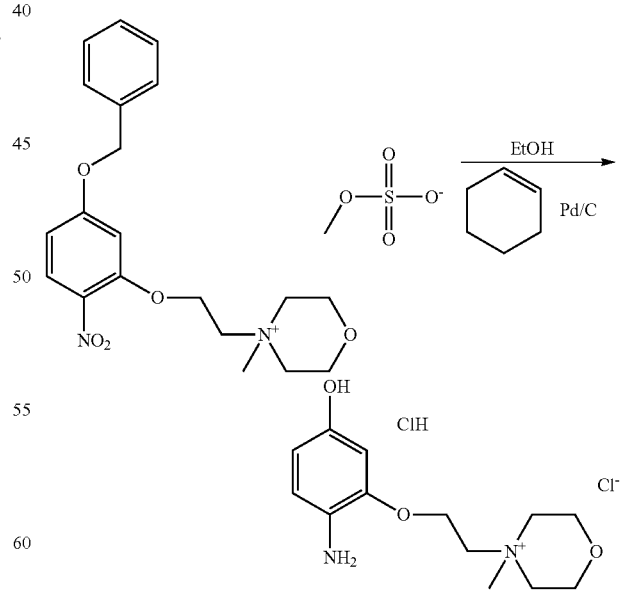

A 500 ml three-necked flask equipped with a thermometer, a condenser and a bubble counter, and with magnetic stirring, is charged successively with 70 ml of ethanol, 19.7 ml of cyclohexene and 2 g of 50% wet 5% palladium-on-charcoal.

This medium is brought to reflux and then a solution of 5 ml of water, 25 ml of ethanol and 6 g (12.43 mmol) of 4-{2-[5-(benzyloxy)-2-nitrophenoxy]ethyl}-4-methyl-morpholin-4-ium methyl sulfate is then added dropwise to the reaction medium. Once the addition is completed, the solution is left under reflux for 5 h.

After cooling under argon, the reaction medium is filtered under a stream of argon through a sintered glass funnel packed with Celite into a vacuum flask containing 25 ml of 6.0N hydrochloric acid in 2-propanol at 0° C.

In the absence of a precipitate, the filtrate is concentrated until a liquor of around 30 ml is obtained. The liquor is taken up in 200 ml of isopropanol and then concentrated again. The operation is repeated until a precipitate appears. The precipitate formed is then filtered on a sintered glass funnel in the presence of argon (highly hygroscopic product), washed with 50 ml of isopropanol then 3×50 ml of diisopropyl ether.

After drying under vacuum at 40° C. in the presence of a desiccant until a constant weight is obtained, 2.4 g of a grey powder corresponding to the expected product are obtained. (Yield=76.2%).

Mass spectrometry analysis confirms the structure of the expected compound. The expected cation $[C_{13}H_{21}N_2C_3]^+$ is mainly detected.

Examples 4 to 7 are carried out in an identical manner to Example 1, namely substitution using the corresponding alcoholate, cationization and reduction.

Example 4

Synthesis of 4-(2-amino-5-hydroxyphenyl)-1,1-dimethylpiperazin-1-ium chloride hydrochloride

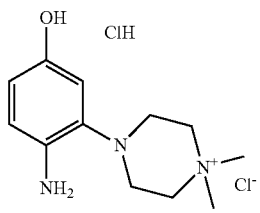 [SMILES: C[N+]1(C)CCN(c2cc(O)ccc2N)CC1 ; Cl ; [Cl-]]

Synthesis of 3-(4-methylpiperazin-1-yl)-4-nitrophenol

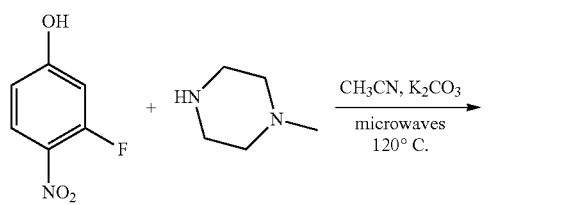

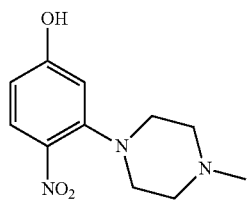

An 80 ml microwave reactor is successively charged with 40 ml of acetonitrile, 5 g (31.82 mmol) of 3-fluoro-4-nitrophenol, 5.27 g (38.19 mmol) of potassium carbonate and 3.9 ml (35 mmol) of 1-methylpiperazine.

This medium is irradiated at 110° C. for 90 minutes. After cooling the medium is filtered through a sintered funnel and the solvent is evaporated until a yellow solid is obtained.

This crude product is purified by chromatography on a silica column, eluent=MeOH/CH$_2$Cl$_2$.

After evaporation of the solvents, 6.76 g (89.5% yield) of an orange powder corresponding to the expected product are obtained.

Mass spectrometry analysis confirms the structure of the expected compound, $C_{11}H_{15}N_3C_3$ is mainly detected.

The quasi-molecular ions [M+H]$^+$, [M+Na]$^+$, [M−H]$^−$ of the expected molecule are mainly detected.

Synthesis of 4-(5-hydroxy-2-nitrophenyl)-1,1-dimethylpiperazin-1-ium methyl sulfate

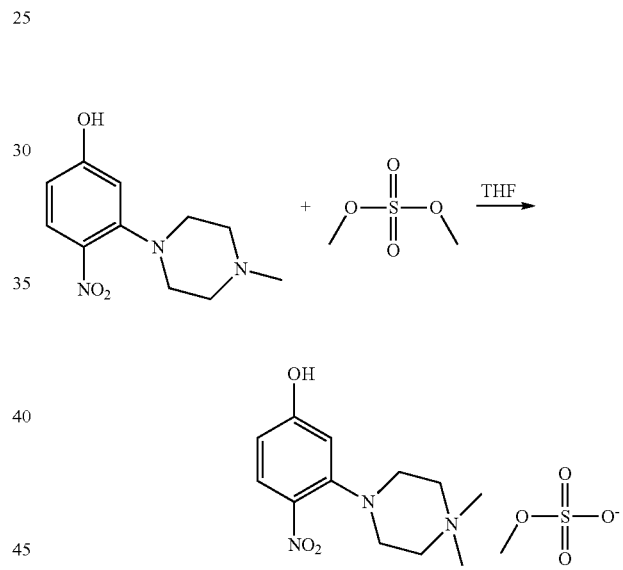

A 100 ml three-necked flask equipped with a thermometer, a condenser, a bubble counter and a dropping funnel, and with magnetic stirring, is charged successively with 40 ml of THF and 4 g (16.86 mmol) of 3-(4-methylpiperazin-1-yl)-4-nitrophenol. Next, added dropwise are 1.7 ml (17.67 mmol) of dimethyl sulfate and the whole assembly continues to be stirred at room temperature for 3 hours.

The yellow solid formed is filtered off on a sintered glass funnel, drained by suction, washed with THF and then dried under vacuum at 50° C. in the presence of a desiccant until a constant weight is obtained. 5.87 g (95.9% yield) of the expected compound are thus isolated in the form of a yellow solid.

Mass spectrometry analysis confirms the structure of the expected compound. The expected cation $[C_{12}H_{18}N_3O_3]^+$ is mainly detected.

Synthesis of 4-(2-amino-5-hydroxyphenyl)-1,1-dimethylpiperazin-1-ium

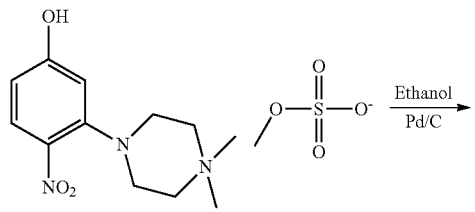

This reduction is carried out using a hydrogenation reactor of H-Cube type containing a 90×4 mm cartridge of 10% Pd/C.

A solution resulting from 1.51 g (4.21 mmol) of 4-(5-hydroxy-2-nitrophenyl)-1,1-dimethylpiperazin-1-ium methyl sulfate, 20 ml of water and 85 ml of ethanol is introduced under a flow rate of 1 ml per minute through a catalyst cartridge within the H-Cube system.

On leaving the device, the expected compound is isolated by precipitation in 50 ml of 6N hydrochloric acid in isopropanol.

The solid formed is drained by suction on a sintered funnel and washed with 2×20 ml of isopropanol and 2×30 ml of diisopropyl ether.

After drying under vacuum at 30° C. in the presence of a desiccant, 834 mg (44.6% yield) of the expected compound are obtained in the form of a white solid.

Mass spectrometry analysis confirms the structure of the expected compound. The expected cation $[C_{12}H_{20}N_3O]^+$ is mainly detected.

Examples of Dyeing

The following dye compositions are prepared:

Example 1

| | | | | |
|---|---|---|---|---|
| 2-(2-amino-5-hydroxy-phenoxy)-N,N,N-trimethyl-ethanaminium chloride dihydrochloride | $10^{-3}$ mol | | | |
| 3-amino-2-chloro-6-methylphenol | | $10^{-3}$ mol | | |
| 2-methyl-5-hydroxy-ethylaminophenol | | | $10^{-3}$ mol | |
| 3,4-dihydro-2H-1,4-benzoxazin-6-ol | | | | |
| 2-(2,4-diamino-phenoxy)-ethanol hydrochloride | | | | $10^{-3}$ mol |
| Dye support (1) | () | () | () | () |
| Demineralized water qs | 100 g | 100 g | 100 g | 100 g |
| Shade observed | pearly pink | golden blonde | matt green grey | beige brown |

Example 2

| | | | | |
|---|---|---|---|---|
| 4-(3,5-diaminopyridin-2-yl)-1,1-dimethyl-piperazin-1-ium chloride hydrochloride | $10^{-3}$ mol | | | |
| 3-amino-2-chloro-6-methylphenol | | $10^{-3}$ mol | | |
| 2-methyl-5-hydroxy-ethylaminophenol | | | $10^{-3}$ mol | |
| 3,4-dihydro-2H-1,4-benzoxazin-6-ol | | | | |
| 2-(2,4-diamino-phenoxy)-ethanol hydrochloride | | | | $10^{-3}$ mol |
| Dye support (1) | () | () | () | () |
| Demineralized water qs | 100 g | 100 g | 100 g | 100 g |
| Shade observed | dark pearly pink | pearly blonde | bluish grey | brown |

Example 3

| | | | | |
|---|---|---|---|---|
| 4-amino-3-[2-(morpholin-4-yl)ethoxy]phenol chloride hydrochloride | $10^{-3}$ mol | | | |
| 3-amino-2-chloro-6-methylphenol | | $10^{-3}$ mol | | |
| 2-methyl-5-hydroxy-ethylaminophenol | | | $10^{-3}$ mol | |
| 3,4-dihydro-2H-1,4-benzoxazin-6-ol | | | | |
| 2-(2,4-diamino-phenoxy)-ethanol hydrochloride | | | | $10^{-3}$ mol |
| Dye support (1) | () | () | () | () |
| Demineralized water qs | 100 g | 100 g | 100 g | 100 g |
| Shade observed | matt pearly pink | gold | grey | brown |

Example 4

| | |
|---|---|
| 4-(2-amino-5-hydroxyphenyl)-1,1-dimethyl-piperazin-1-ium chloride hydrochloride | $10^{-3}$ mol |
| 3-amino-2-chloro-6-methylphenol | $10^{-3}$ mol |
| 2-methyl-5-hydroxy-ethylaminophenol | $10^{-3}$ mol |
| 3,4-dihydro-2H-1,4-benzoxazin-6-ol | $10^{-3}$ mol |
| 2-(2,4-diamino-phenoxy)-ethanol hydrochloride | $10^{-3}$ mol |

| Dye support (1) | () | () | (**) | (*) |
|---|---|---|---|---|
| Demineralized water qs | 100 g | 100 g | 100 g | 100 g |
| Shade observed | brown pearly pink | golden brown | light gold | beige |

(**): dye support (1) pH 9.5

| 96° ethyl alcohol | 20.8 g | |
|---|---|---|
| 35% aqueous sodium metabisulfite solution | 0.23 g | AM |
| Pentasodium salt of diethylenetriaminepentaacetic acid as an aqueous 40% solution | 0.48 g | AM |
| C8-C10 alkyl polyglucoside as an aqueous 60% solution | 3.6 g | AM |
| Benzyl alcohol | 2.0 g | |
| Polyethylene glycol containing 8 units of ethylene oxide | 3.0 g | |
| NH$_4$Cl | 4.32 g | |
| Aqueous ammonia containing 20% NH$_3$ | 2.94 g | |

At the time of use, each composition is mixed with an equal weight of 20-volumes aqueous hydrogen peroxide solution (6% by weight). A final pH of 9.5 is obtained. Each mixture obtained is applied to locks of grey hair containing 90% white hairs. After a leave-in time of 30 minutes, the locks are rinsed, washed with a standard shampoo, rinsed again and then dried, to give the shades mentioned.

The invention claimed is:

1. A dye composition for dyeing keratin fibers comprising, in a medium that is suitable for dyeing keratin fibers, at least one para-Aminophenol compound of formula (I), the addition salts thereof with an acid, and the solvates thereof:

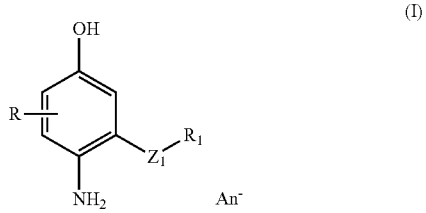

(I)

wherein:
R is chosen from a hydrogen atom, a halogen atom, a C$_1$-C$_4$ alkyl radical, a carboxyl radical, and a (C$_1$-C$_4$) alkoxycarbonyl radical;
Z1 is chosen from an oxygen atom and a group NR2;
R2 is chosen from a hydrogen atom, a linear or branched C$_1$-C$_4$ alkyl radical, a benzyl radical, and an acetyl radical;
R1 is chosen from a saturated, linear or branched C$_1$-C$_{10}$ alkyl radical, which is substituted with or interrupted by a cationic radical; or a saturated, unsaturated or aromatic cationic 5- to 8-membered heterocycle;
with the proviso that when Z1 represents NR2, then R1 and R2 may form, together with the nitrogen atom to which they are attached, a saturated or unsaturated cationic 5- to 8-membered heterocycle; or a saturated or unsaturated noncationic 5- to 8-membered heterocycle substituted with a cationic radical; and
An$^-$ represents an anion or a mixture of anions which are organic or inorganic and are cosmetically acceptable.

2. The dye composition according to claim 1, wherein R1 is a saturated, linear or branched C$_1$-C$_{10}$ alkyl radical, which is interrupted by at least one oxygen atom and/or by at least one group NR2, and/or substituted with at least one radical chosen from hydroxyl, alkoxy or C$_1$-C$_4$ hydroxyalkyl radicals; or a saturated, unsaturated or aromatic cationic 5- to 8-membered heterocycle substituted with at least one radical chosen from C$_1$-C$_4$ alkyl, hydroxyl, C$_1$-C$_4$ alkoxy, amino, (C$_1$-C$_4$)alkylamino, di(C$_1$-C$_4$)alkylamino, thio, (C$_1$-C$_4$)alkylthio, carboxyl, (C$_1$-C$_4$)alkylcarbonyl, sulfonyl, amido or C$_1$-C$_4$ hydroxyalkyl radicals.

3. The dye composition according to claim 1, wherein when Z1 is NR2, then R1 and R2 form, together with the nitrogen atom to which they are attached, a saturated or unsaturated cationic 5- to 8-membered heterocycle substituted with at least one radical chosen from C$_1$-C$_{10}$ alkyl radicals and hydroxyl, C$_1$-C$_4$ alkoxy, amino, (C$_1$-C$_4$)alkylamino, di(C$_1$-C$_4$)alkylamino, thio, (C$_1$-C$_4$)alkylthio, carboxyl, (C$_1$-C$_4$)alkylcarbonyl, sulfonyl, amido and C$_1$-C$_4$ hydroxyalkyl radicals, wherein the heterocycle includes at least one heteroatom chosen from N or O; or a saturated or unsaturated noncationic 5- to 8-membered heterocycle substituted with at least one radical chosen from C$_1$-C$_{10}$ alkyl radicals and hydroxyl, C$_1$-C$_4$ alkoxy, amino, (C$_1$-C$_4$)alkylamino, di(C$_1$-C$_4$)alkylamino, thio, (C$_1$-C$_4$)alkylthio, carboxyl, (C$_1$-C$_4$) alkylcarbonyl, sulfonyl, amido and C$_1$-C$_4$ hydroxyalkyl radicals.

4. The dye composition according to claim 1, wherein the cationic radical is a linear or branched or heterocyclic radical comprising a quaternary ammonium, the quaternary ammonium being of the type —N$^+$RaRbRc, wherein Ra, Rb and Rc, which may be identical or different, are chosen from a C$_1$-C$_6$ alkyl radical.

5. The dye composition according to claim 4, wherein the C$_1$-C$_6$ alkyl radical is substituted with a hydroxyl;
with the proviso that when Ra and Rb form a 5- to 8-membered heterocycle, the radical Rc is a C$_1$-C$_6$ alkyl radical optionally substituted with a hydroxyl.

6. The dye composition according to claim 1 wherein:
R is chosen from a hydrogen atom and a C$_1$-C$_4$ alkyl radical;
Z1 is chosen from an oxygen atom and a group NR2, wherein R2 is chosen from a hydrogen atom and a C$_1$-C$_2$ alkyl radical;
R1 is chosen from a linear or branched C$_1$-C$_8$ alkyl radical, which is substituted with or interrupted by a cationic radical; or a saturated, unsaturated or aromatic cationic 5- to 8-membered heterocycle.

7. The dye composition according to claim 6, wherein:
R is a hydrogen atom;
R2 is chosen from a hydrogen atom and CH$_3$;
R1 is chosen from a linear or branched C$_1$-C$_8$ alkyl radical interrupted by at least one oxygen atom and/or by at least one group NR2, and/or substituted with a hydroxyl radical,
wherein said cationic radical is substituted with at least one radical chosen from C$_1$-C$_4$ alkyl or C$_1$-C$_4$ alkoxy radicals; or a saturated, unsaturated or aromatic cationic 5- to 8-membered heterocycle substituted with at least one radical chosen from C$_1$-C$_4$ alkyl, hydroxyl, C$_1$-C$_4$ alkoxy, amino, (C$_1$-C$_4$)alkylamino, di(C$_1$-C$_4$)alkylamino, thio, (C$_1$-C$_4$)alkylthio, carboxyl, (C$_1$-C$_4$)alkylcarbonyl, sulfonyl, amido or C$_1$-C$_4$ hydroxyalkyl radicals.

8. The dye composition according to claim 1 wherein:
R is chosen from a hydrogen atom and a C$_1$-C$_4$ alkyl radical;
Z1 represents NR2; and
R1 and R2 form, together with the nitrogen atom to which they are attached, a saturated or unsaturated noncationic 5- to 8-membered heterocycle substituted with a cationic radical.

9. The dye composition according to claim 8 wherein:
R is a hydrogen atom; and
R1 and R2 form, together with the nitrogen atom to which they are attached, a saturated or unsaturated noncationic 5- to 8-membered heterocycle substituted with a cationic radical and substituted with at least one radical chosen from $C_1$-$C_{10}$ alkyl radicals and hydroxyl, $C_1$-$C_4$ alkoxy, amino, ($C_1$-$C_4$)alkylamino, di($C_1$-$C_4$)alkylamino, ($C_1$-$C_4$)alkylcarbonyl, amido and $C_1$-$C_4$ hydroxyalkyl radicals.

10. The dye composition according to claim 1, wherein Z1 represents NR2, and R1 and R2 form, together with the nitrogen atom to which they are attached, a noncationic heterocycle chosen from pyrrolidine, piperidine, morpholine, and mixtures thereof.

11. The dye composition according to claim 1, wherein at least one of R1 and a saturated or unsaturated cationic 5- to 8-membered heterocycle formed by R1 and R2 are substituted with or interrupted by a cationic radical chosen from trimethylammonium, triethylammonium, dimethylethylammonium, diethylmethylammonium, diisopropylmethylammonium, hydroxyethyldiethylammonium, imidazolium, pyridinium, piperazinium, pyrrolidinium, morpholinium, pyrimidinium, thiazolium, benzimidazolium and piperidinium radicals and mixtures thereof.

12. The dye composition according to claim 1, wherein:
R represents a hydrogen atom or a $C_1$-$C_4$ alkyl radical;
Z1 represents NR2; and
R1 and R2 form, together with the nitrogen atom to which they are attached, a saturated or unsaturated cationic 5- to 8-membered heterocycle.

13. The dye composition according to claim 12, wherein:
R represents a hydrogen atom; and
R1 and R2 form, together with the nitrogen atom to which they are attached, a saturated or unsaturated cationic 5- to 8-membered heterocycle substituted with at least one radical chosen from $C_1$-$C_{10}$ alkyl radicals and hydroxyl, $C_1$-$C_4$ alkoxy, amino, ($C_1$-$C_4$)alkylamino, di($C_1$-$C_4$) alkylamino, ($C_1$-$C_4$)alkylcarbonyl, amido and $C_1$-$C_4$ hydroxyalkyl radicals.

14. The dye composition according to claim 12, wherein the heterocycle contains at least one heteroatom chosen from N and O.

15. The dye composition according to claim 12, wherein the cationic heterocycle is chosen from imidazolium, pyridinium, piperidinium, piperazinium, pyrrolidinium, morpholinium, pyrimidinium, thiazolium, benzimidazolium, benzothiazolium and oxazolium radicals and combinations thereof.

16. The dye composition according to claim 1, wherein the compound is chosen from:
2-(2-amino-5-hydroxyphenoxy)-N,N,N-trimethylethanaminium, An⁻,
1-[2-(2-amino-5-hydroxyphenoxy)ethyl]-1-methylpiperidinium, An⁻,
1-[2-(2-amino-5-hydroxyphenoxy)ethyl]-1-methylpyrrolidinium, An⁻,
4-[2-(2-amino-5-hydroxyphenoxy)ethyl]-4-methylmorpholin-4-ium, An⁻,
1-[2-(2-amino-5-hydroxyphenoxy)ethyl]-3-methyl-1H-imidazol-3-ium, An⁻,
4-[2-(2-amino-5-hydroxyphenoxy)ethyl]-1,1-dimethylpiperazin-1-ium, An⁻,
3-(2-amino-5-hydroxyphenoxy)-N,N,N-trimethylpropan-1-aminium, An⁻,
1-[3-(2-amino-5-hydroxyphenoxy)propyl]-1-methylpiperidinium, An⁻,
1-[3-(2-amino-5-hydroxyphenoxy)propyl]-1-methylpyrrolidinium, An⁻,
4-[3-(2-amino-5-hydroxyphenoxy)propyl]-4-methylmorpholin-4-ium, An⁻,
1-[3-(2-amino-5-hydroxyphenoxy)propyl]-3-methyl-1H-imidazol-3-ium, An⁻,
4-[3-(2-amino-5-hydroxyphenoxy)propyl]-1,1-dimethylpiperazin-1-ium, An⁻,
2-[(2-amino-5-hydroxyphenyl)amino]-N,N,N-trimethylethanaminium, An⁻,
4-{2-[(2-amino-5-hydroxyphenyl)amino]ethyl}-1,1-dimethylpiperazin-1-ium, An⁻,
4-{2-[(2-amino-5-hydroxyphenyl)amino]ethyl}-1-(2-hydroxyethyl)-1-methylpiperazin-1-ium, An⁻,
1-{3-[(2-amino-5-hydroxyphenyl)amino]propyl}-1-methylpiperidinium, An⁻,
1-{3-[(2-amino-5-hydroxyphenyl)amino]propyl}-1-methylpyrrolidinium, An⁻,
4-{3-[(2-amino-5-hydroxyphenyl)amino]propyl}-4-methylmorpholin-4-ium, An⁻,
1-{3-[(2-amino-5-hydroxyphenyl)amino]propyl}-3-methyl-1H-imidazol-3-ium, An⁻,
3-[(2-amino-5-hydroxyphenyl)(methyl)amino]-N,N,N-trimethylpropan-1-aminium, An⁻,
1-{3-[(2-amino-5-hydroxyphenyl)(methyl)amino]propyl}-1-methylpyrrolidinium, An⁻,
1-{3-[(2-amino-5-hydroxyphenyl)(methyl)amino]propyl}-1-methylpiperidinium, An⁻,
4-{3-[(2-amino-5-hydroxyphenyl)(methyl)amino]propyl}-4-methylmorpholin-4-ium, An⁻,
4-(2-amino-5-hydroxyphenyl)-1,1-dimethylpiperazin-1-ium, An⁻,
4-(2-amino-5-hydroxyphenyl)-1,1-bis(2-hydroxyethyl)piperazin-1-ium, An⁻,
1-[2-({2-[(2-amino-5-hydroxyphenyl)amino]ethyl}amino)ethyl]-1-methylpiperidinium, An⁻,
1-[2-({2-[(2-amino-5-hydroxyphenyl)amino]ethyl}amino)ethyl]-3-methyl-1H-imidazol-3-ium, An⁻,
2-({2-[(2-amino-5-hydroxyphenyl)amino]ethyl}amino)-N,N,N-trimethylethanaminium, An⁻,
2-{2-[(2-amino-5-hydroxyphenyl)amino]ethoxy}-N,N,N-trimethylethanaminium, An⁻,
1-(2-{2-[(2-amino-5-hydroxyphenyl)amino]ethoxy}ethyl)-1-methylpiperidinium, An⁻,
4-(2-{2-[(2-amino-5-hydroxyphenyl)amino]ethoxy}ethyl)-1,1-dimethylpiperazin-1-ium, An⁻,
4-(2-{2-[(2-amino-5-hydroxyphenyl)amino]ethoxy}ethyl)-4-methylmorpholin-4-ium, An⁻,
3-[(2-amino-5-hydroxyphenyl)amino]-N,N,N-trimethylpropan-1-aminium, An⁻,
4-{3-[(2-amino-5-hydroxyphenyl)amino]propyl}-1,1-dimethylpiperazin-1-ium, An⁻,
1-{2-[(2-amino-5-hydroxyphenyl)amino]ethyl}-1-methylpiperidinium, An⁻,
1-{2-[(2-amino-5-hydroxyphenyl)amino]ethyl}-1-methylpyrrolidinium, An⁻,
4-{2-[(2-amino-5-hydroxyphenyl)amino]ethyl}-4-methylmorpholin-4-ium, An⁻,
1-{2-[(2-amino-5-hydroxyphenyl)amino]ethyl}-3-methyl-1H-imidazol-3-ium, An⁻,
2-[(2-amino-5-hydroxyphenyl)(methyl)amino]-N,N,N-trimethylethanaminium, An⁻,
1-{2-[(2-amino-5-hydroxyphenyl)(methyl)amino]ethyl}-1-methylpyrrolidinium, An⁻,
1-{2-[(2-amino-5-hydroxyphenyl)(methyl)amino]ethyl}-1-methylpiperidinium, An⁻, 4-{2-[(2-amino-5-hydroxyphenyl)(methyl)amino]ethyl}-4-methylmorpholin-4-ium, An⁻, 1-(2-amino-5-hydroxyphenyl)-N,N,N-trimethylpyrrolidin-3-aminium, An⁻, 4-(2-amino-5-hydroxyphenyl)-1-(2-hydroxyethyl)-1-methylpiperazin-1-ium, An⁻, 1-[2-({2-[(2-amino-5-hydroxyphenyl)amino]ethyl}amino)ethyl]-1-methylpyrrolidinium, An⁻, 4-[2-({2-[(2-amino-5-hydroxyphenyl)amino]ethyl}amino)ethyl]-4-methylmorpholin-4-ium, An⁻, 3-({2-[(2-amino-5-hydroxyphenyl)amino]ethyl}amino)-N,N,N-trimethylpropan-1-aminium, An⁻, 3-{2-[(2-amino-5-hydroxyphenyl)amino]ethoxy}-N,N,N-trimethylpropan-1-aminium, An⁻, 1-(2-{2-[(2-amino-5-hydroxyphenyl)amino]ethoxy}ethyl)-1-methylpyrrolidinium, An⁻, 4-(3-{2-[(2-amino-5-hydroxyphenyl)amino]ethoxy}propyl)-1,1-dimethylpiperazin-1-ium, An⁻, 4-(3-{2-[(2-amino-5-hydroxyphenyl)amino]ethoxy}propyl)-4-methylmorpholin-4-ium, An⁻, the addition salts thereof with an acid and/or solvates thereof, and mixtures thereof.

17. A method for dyeing keratin fibers, the method comprising:

applying to the keratin fibers in the presence of at least one oxidizing agent for a period of time sufficient to develop the desired coloring, a para-Aminophenol compound of formula (I), the addition salts thereof with an acid, and the solvates thereof:

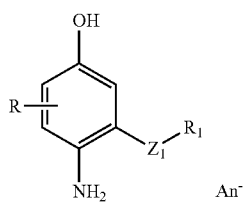

wherein:
R is chosen from a hydrogen or halogen atom; a $C_1$-$C_4$ alkyl radical; a carboxyl radical; and a ($C_1$-$C_4$) alkoxycarbonyl radical;

Z1 is chosen from an oxygen atom and a group NR2;

R2 is chosen from a hydrogen atom, a linear or branched $C_1$-$C_4$ alkyl radical, a benzyl radical, and an acetyl radical;

R1 is chosen from a saturated, linear or branched $C_1$-$C_{10}$ alkyl radical, which is substituted with or interrupted by a cationic radical;

or a saturated, unsaturated or aromatic cationic 5- to 8-membered heterocycle;

with the proviso when Z1 represents NR2 then
R1 and R2 may form, together with the nitrogen atom to which they are attached, a saturated or unsaturated cationic 5- to 8-membered heterocycle; or a saturated or unsaturated noncationic 5- to 8-membered heterocycle substituted with a cationic radical; and An⁻ represents an anion or a mixture of anions which are organic or inorganic and are cosmetically acceptable.

18. A multi-compartment device comprising a first compartment configured to contain the dye composition according to claim 1 and a second compartment configured to contain at least one oxidizing agent.

19. The dye composition according claim 1 further comprising an oxidizing agent chosen from hydrogen peroxide, urea peroxide, alkali metal bromates, persalts, peracids and oxidase enzymes.

20. The method according to claim 17, wherein the compound is chosen from:

2-(2-amino-5-hydroxyphenoxy)-N,N,N-trimethylethanaminium, An⁻,

1-[2-(2-amino-5-hydroxyphenoxy)ethyl]-1-methylpiperidinium, An⁻,

1-[2-(2-amino-5-hydroxyphenoxy)ethyl]-1-methylpyrrolidinium, An⁻,

4-[2-(2-amino-5-hydroxyphenoxy)ethyl]-4-methylmorpholin-4-ium, An⁻,

1-[2-(2-amino-5-hydroxyphenoxy)ethyl]-3-methyl-1H-imidazol-3-ium, An⁻,

4-[2-(2-amino-5-hydroxyphenoxy)ethyl]-1,1-dimethylpiperazin-1-ium, An⁻, 3-(2-amino-5-hydroxyphenoxy)-N,N,N-trimethylpropan-1-aminium, An⁻, 1-[3-(2-amino-5-hydroxyphenoxy)propyl]-1-methylpiperidinium, An⁻, 1-[3-(2-amino-5-hydroxyphenoxy)propyl]-1-methylpyrrolidinium, An⁻, 4-[3-(2-amino-5-hydroxyphenoxy)propyl]-4-methylmorpholin-4-ium, An⁻, 1-[3-(2-amino-5-hydroxyphenoxy)propyl]-3-methyl-1H-imidazol-3-ium, An⁻, 4-[3-(2-amino-5-hydroxyphenoxy)propyl]-1,1-dimethylpiperazin-1-ium, An⁻, 2-[(2-amino-5-hydroxyphenyl)amino]-N,N,N-trimethylethanaminium, An⁻, 4-{2-[(2-amino-5-hydroxyphenyl)amino]ethyl}-1,1-dimethylpiperazin-1-ium, An⁻, 4-{2-[(2-amino-5-hydroxyphenyl)amino]ethyl}-1-(2-hydroxyethyl)-1-methylpiperazin-1-ium, An⁻, 1-{3-[(2-amino-5-hydroxyphenyl)amino]propyl}-1-methylpiperidinium, An⁻, 1-{3-[(2-amino-5-hydroxyphenyl)amino]propyl}-1-methylpyrrolidinium, An⁻, 4-{3-[(2-amino-5-hydroxyphenyl)amino]propyl}-4-methylmorpholin-4-ium, An⁻, 1-{3-[(2-amino-5-hydroxyphenyl)amino]propyl}-3-methyl-1H-imidazol-3-ium, An⁻, 3-[(2-amino-5-hydroxyphenyl)(methyl)amino]-N,N,N-trimethylpropan-1-aminium, An⁻, 1-{3-[(2-amino-5-hydroxyphenyl)(methyl)amino]propyl}-1-methylpyrrolidinium, An⁻, 1-{3-[(2-amino-5-hydroxyphenyl)(methyl)amino]propyl}-1-methylpiperidinium, An⁻, 4-{3-[(2-amino-5-hydroxyphenyl)(methyl)amino]propyl}-4-methylmorpholin-4-ium, An⁻, 4-(2-amino-5-hydroxyphenyl)-1,1-dimethylpiperazin-1-ium, An⁻, 4-(2-amino-5-hydroxyphenyl)-1,1-bis(2-hydroxyethyl)piperazin-1-ium, An⁻, 1-[2-({2-[(2-amino-5-hydroxyphenyl)amino]ethyl}amino)ethyl]-1-methylpiperidinium, An⁻, 1-[2-({2-[(2-amino-5-hydroxyphenyl)amino]ethyl}amino)ethyl]-3-methyl-1H-imidazol-3-ium, An⁻, 2-({2-[(2-amino-5-hydroxyphenyl)amino]ethyl}amino)-N,N,N-trimethylethanaminium, An⁻, 2-{2-[(2-amino-5-hydroxyphenyl)amino]ethoxy}-N,N,N-trimethylethanaminium, An⁻, 1-(2-{2-[(2-amino-5-hydroxyphenyl)amino]ethoxy}ethyl)-1-methylpiperidinium, An⁻, 4-(2-{2-[(2-amino-5-hydroxyphenyl)amino]ethoxy}ethyl)-1,1-dimethylpiperazin-1-ium, An⁻, 4-(2-{2-[(2-amino-5-hydroxyphenyl)amino]ethoxy}ethyl)-4-methylmorpholin-4-ium, An⁻, 3-[(2-amino-5-hydroxyphenyl)amino]-N,N,N-trimethylpropan-1-aminium, An⁻, 4-{3-[(2-amino-5-hydroxyphenyl)amino]propyl}-1,1-dimethylpiperazin-1-ium, An⁻, 1-{2-[(2-amino-5-hydroxyphenyl)amino]ethyl}-1-methylpiperidinium, An⁻, 1-{2-[(2-amino-5-hydroxyphenyl)amino]ethyl}-1-methylpyrrolidinium, An⁻, 4-{2-[(2-amino-5-hydroxyphenyl)amino]ethyl}-4-methylmorpholin-4-ium, An⁻, 1-{2-[(2-amino-5-hydroxyphenyl)amino]ethyl}-3-methyl-1H-imidazol-3-ium, An⁻, 2-[(2-amino-5-hydroxyphenyl)(methyl)amino]-N,N,N-trimethylethanaminium, An⁻, 1-{2-[(2-amino-5-hydroxyphenyl)(methyl)amino]ethyl}-1-methylpyrrolidinium, An⁻, 1-{2-[(2-amino-5-hydroxyphenyl)(methyl)amino]ethyl}-1-methylpiperidinium, An⁻, 4-{2-[(2-amino-5-hydroxyphenyl)(methyl)amino]ethyl}-4-methylmorpholin-4-ium, An⁻, 1-(2-amino-5-hydroxyphenyl)-N,N,N-trimethylpyrrolidin-3-aminium, An⁻, 4-(2-amino-5-hydroxyphenyl)-1-(2-hydroxyethyl)-1-methylpiperazin-1-ium, An⁻, 1-[2-({2-[(2-amino-5-hydroxyphenyl)amino]ethyl}amino)ethyl]-1-methylpyrrolidinium, An⁻, 4-[2-({2-[(2-amino-5-hydroxyphenyl)amino]ethyl}amino)ethyl]-4-methylmorpholin-4-ium, An⁻, 3-({2-[(2-amino-5-hydroxyphenyl)amino]ethyl}amino)-N,N,N-trimethylpropan-1-aminium, An⁻, 3-{2-[(2-amino-5-hydroxyphenyl)amino]ethoxy}-N,N,N-trimethylpropan-1-aminium, An⁻, 1-(2-{2-[(2-amino-5-hydroxyphenyl)amino]ethoxy}ethyl)-1-methylpyrrolidinium, An⁻, 4-(3-{2-[(2-amino-5-hydroxyphenyl)amino]ethoxy}propyl)-1,1-dimethylpiperazin-1-ium, An⁻, 4-(3-{2-[(2-amino-5-hydroxyphenyl)amino]ethoxy}propyl)-4-methylmorpholin-4-ium, An⁻, the addition salts thereof with an acid and/or solvates thereof, and mixtures thereof.

21. The method according to claim 17, further comprising applying an oxidizing agent chosen from hydrogen peroxide, urea peroxide, alkali metal bromates, persalts, peracids and oxidase enzymes to said keratin fibers.

* * * * *